(12) United States Patent
Friedman et al.

(10) Patent No.: US 11,978,121 B1
(45) Date of Patent: May 7, 2024

(54) SYSTEM AND METHOD FOR ENABLING REAL-TIME ITERATIVE COLLABORATIVE DECISION SUPPORT

(71) Applicant: Nationwide Mutual Insurance Company, Columbus, OH (US)

(72) Inventors: Zachary M. Friedman, Columbus, OH (US); Sumeet P. Singh, Hilliard, OH (US); Marcus Hitt, Worthington, OH (US); Richard W. Burchfield, New Albany, OH (US); Debra Rosen, Lewis Center, OH (US); Matthew Westlake, Pataskala, OH (US); Calvin Goodman, Columbus, OH (US)

(73) Assignee: Nationwide Mutual Insurance Company, Columbus, OH (US)

( * ) Notice: Subject to any disclaimer, the term of this patent is extended or adjusted under 35 U.S.C. 154(b) by 0 days.

(21) Appl. No.: 17/948,415

(22) Filed: Sep. 20, 2022

Related U.S. Application Data

(63) Continuation of application No. 16/903,745, filed on Jun. 17, 2020, now Pat. No. 11,455,689.

(60) Provisional application No. 63/021,941, filed on May 8, 2020.

(51) Int. Cl.
| | |
|---|---|
| *G06Q 40/06* | (2012.01) |
| *G06F 9/451* | (2018.01) |
| *G06Q 30/016* | (2023.01) |
| *G16H 80/00* | (2018.01) |
| *G06F 3/0481* | (2022.01) |
| *H04L 65/403* | (2022.01) |

(52) U.S. Cl.
CPC .............. *G06Q 40/06* (2013.01); *G06F 9/453* (2018.02); *G06Q 30/016* (2013.01); *G16H 80/00* (2018.01); *G06F 3/0481* (2013.01); *H04L 65/403* (2013.01)

(58) Field of Classification Search
CPC .............................. G06Q 40/06; G16H 80/00
See application file for complete search history.

(56) References Cited

U.S. PATENT DOCUMENTS

| | | | |
|---|---|---|---|
| 9,112,849 B1 | 8/2015 | Werkelin Ahlin et al. | |
| 10,028,205 B2 * | 7/2018 | Agarwal | H04W 74/002 |
| 10,409,625 B1 * | 9/2019 | Suryanarayanan | G06F 8/656 |
| 10,616,278 B1 | 4/2020 | Johansson et al. | |
| 10,817,935 B1 * | 10/2020 | Joglekar | G06Q 40/03 |

(Continued)

*Primary Examiner* — Scott C Anderson
(74) *Attorney, Agent, or Firm* — Morgan, Lewis & Bockius LLP

(57) ABSTRACT

A system for enabling real-time iterative collaborative decision support. The system includes one or more processors and memory storing instructions for receiving a connection request from a client device; establishing a first connection with the client device, including populating a first user interface of the client device, wherein the first user interface corresponds to the first workspace; broadcasting availability of the client device to two or more coach devices; in response to the broadcast, receiving a connection request from a first coach device; and in response to receiving the connection request from the first coach device, establishing a second connection with the first coach device, including populating a second user interface of the first coach device, wherein the second user interface corresponds to the first workspace and includes an element not included in the first user interface of the client device.

19 Claims, 19 Drawing Sheets

(56) References Cited

U.S. PATENT DOCUMENTS

| | | |
|---|---|---|
| 2004/0030750 A1 | 2/2004 | Moore et al. |
| 2012/0106728 A1 | 5/2012 | Ghaffari et al. |
| 2016/0125035 A1 | 5/2016 | Hanson et al. |
| 2016/0295167 A1 | 10/2016 | Sakurai |
| 2017/0262807 A1* | 9/2017 | Kolls .................. G06Q 10/101 |
| 2018/0369678 A1* | 12/2018 | Yang .................. A63B 24/0062 |
| 2020/0092519 A1 | 3/2020 | Shin et al. |

* cited by examiner

Client UI 1300

Coach UI 1350

SYSTEM AND METHOD FOR ENABLING REAL-TIME ITERATIVE COLLABORATIVE DECISION SUPPORT

CROSS-REFERENCE TO RELATED APPLICATIONS

This application is a continuation of U.S. patent application Ser. No. 16/903,745 filed Jun. 17, 2020, which claims the benefit of U.S. Provisional Patent Application No. 63/021,941 filed May 8, 2020 entitled "System and Method for Enabling Real-Time Iterative Collaborative Decision Support", each of which is incorporated by reference herein in its entirety.

BACKGROUND

Recent technological advancements in the fields of guidance, advice, and decision support have been focused on the use of software to automate recommendations and manage planning, forecasting, projections, and optimization on behalf of users. These technological advancements have relied on approaches such as machine learning to develop robust algorithms and create a "recommender system" to deliver advice to users. Recommender systems have been utilized in a variety of fields and are most commonly recognized as playlist generators for video and music services like Netflix, YouTube, and Spotify, product recommenders for services such as Amazon, or content recommenders for social media platforms such as Facebook and Twitter. However, these approaches are now being implemented in more complex fields such as personal finance and investing with the rise of "robo-advisors" (e.g., Wealthfront, Betterment) who use algorithms to manage investors' portfolios at a discounted cost to scale and compete in a once human-driven business.

While automated recommender systems may indeed decrease the cost of guidance, an algorithmic approach to more emotionally driven, complex decisions does not make those who are receiving the advice feel confident in the decision they need to make or alleviate their concerns (which can often be unsubstantiated and driven by bias and hearsay). Applying these technologies to fields like financial services, personal counseling, insurance, healthcare, management consulting, operations, education, and so forth, has created a gulf between what customers want and expect and how the industry is approaching the problem. While customers crave the convenience of getting support whenever they need it (i.e., digitally, remotely, on-demand), they increasingly desire help from a live human expert to ensure they are thinking about things the right way and that their preferences and concerns are accounted for. Customers expect the intervention, support, and collaboration from a live human expert to be seamlessly integrated into their digital experiences, yet have the same effectivity as an in-person conversation. This presents a challenge for enabling expert-guided support for complex decisions—as currently available tools are insufficient in supporting a digitally enabled real-time, iterative approach to supporting complex decision making with the help of a real-live expert.

The technical field for enabling remote, real-time decision support and collaboration between an expert and a user has not had the same level of attention and advancement as has the automated recommender systems, which has further increased the aforementioned gulf.

Currently, most experts seeking to help a remote user with decision support share information using a variety of existing remote support technology. Predominantly, the technology used in these applications are screen-sharing and co-browsing. "Screen-sharing" may use web-based communications like Go-to-meeting or Skype. Co-browsing technology may lead to a similar outcome as "screen-sharing." It is designed as a support tool to allow someone in an enterprise contact center to interact with a customer by using the customer's Web browser to view and interact with customers' web browsers to provide guidance.

These technologies are not sufficient to deliver iterative and dynamic collaboration for financial decision making. Rather, they provide a static way to "screen-cast" information to users or "take-over" a user's screen and browse the same content at the same time.

SUMMARY

This application describes a set of real-time coaching and self-service digital tools for expert guided decision making that provide consumers with iterative decision support, things to consider, and validation whenever they need it. The innovations described herein are designed to iteratively help consumers evaluate tradeoffs, check their thinking, and deal with concerns. This helps establish a personalized relationship between users and experts and is implemented in a way users naturally make decisions, rather than being forced to review a report from an expert or run static simulations in self-service digital tools. The implementations described herein enable a stickier, more valuable relationship between a client and an adviser which becomes broader in scope over time.

The inventive concepts are focused on the appropriate pairing of technology with consumer needs and their mental models in an engaging, interactive, ongoing experience that addresses consumer needs as they contemplate complex issues, such as planning for retirement, understanding the financial impact of future events, or managing the financial tradeoffs of different healthcare decisions.

Most advice is designed within the context of planning or goal setting, but that is not how consumers manage their financial lives. For example, a consumer may generate new questions and concerns based on something that happened to a friend, a story the consumer read, or an upcoming decision the consumer may have. Easily accessible live coaching, asynchronous chat, and digital self-service tools support consumers by iteratively working through these questions as they come up, empowering consumers to make confident decisions outside of a traditional plan or goal.

Getting consumers to an expert who is trained to illuminate trade-offs, validate or invalidate concerns, and provide information to consider helps consumers feel comfortable asking follow-up questions, relying on the coach's expertise, and coming back when they have new questions or concerns. This broadens the set of opportunities an advisor might be able to help consumers with and establishes a long-term relationship rooted in trust.

The financial picture created through this collaboration also provides an opportunity to design "mass customization" financial products that can fit to a user's financial picture and eliminate paperwork or generic solutions. The underlying "financial picture" built by this iterative decision-making process helps advisors understand their customers, provide support in a way that matches consumers' mental model (vs. the industry's fixed views), and provide new avenues for delivering unique financial products custom-tailored to consumers' pictures.

BRIEF DESCRIPTION OF THE DRAWINGS

So that the present disclosure can be understood in greater detail, features of various embodiments are illustrated in the appended drawings. The appended drawings, however, merely illustrate pertinent features of the present disclosure and are therefore not limiting.

DETAILED DESCRIPTION

Figure 1:
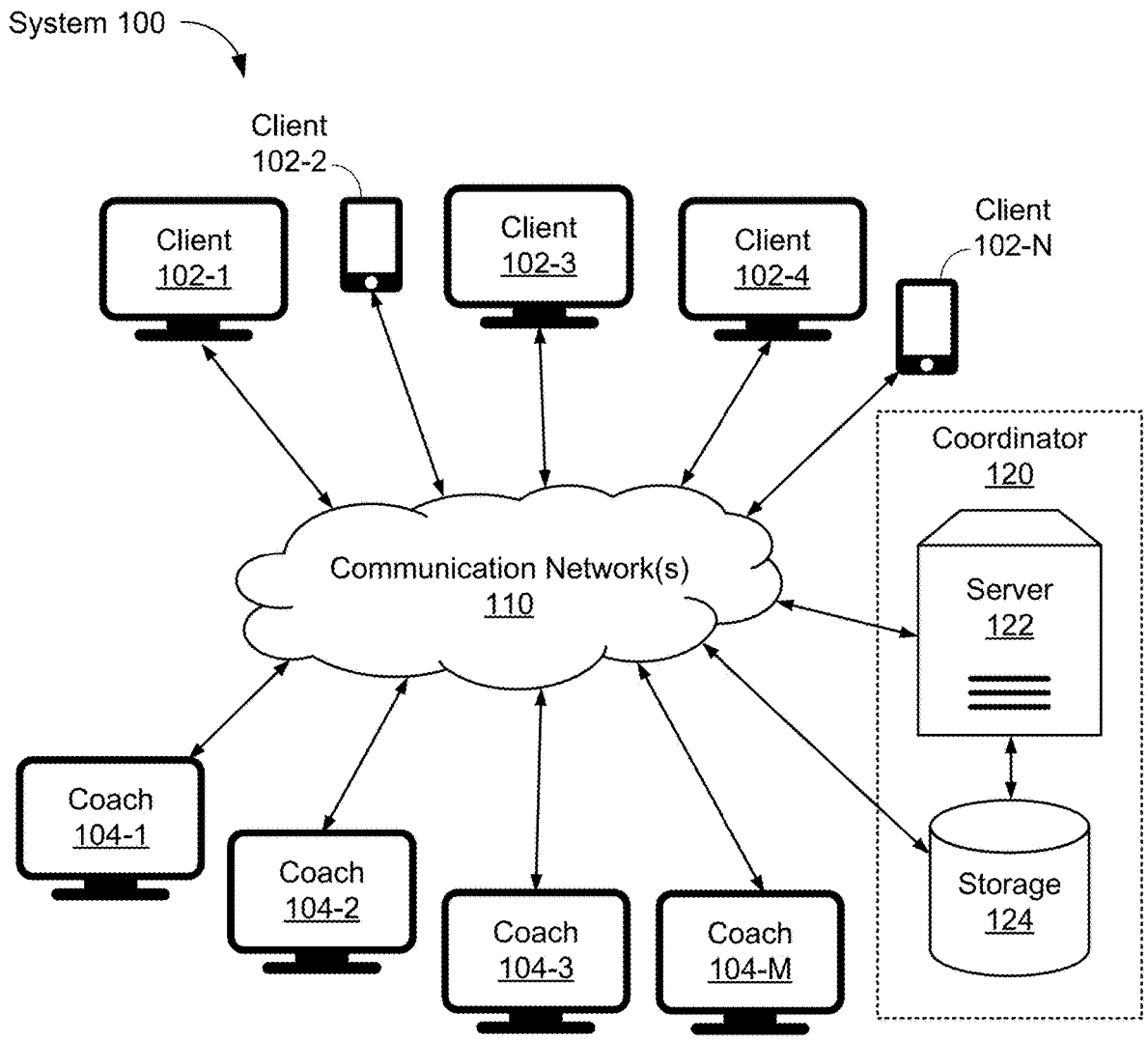
FIG. 1 is a system diagram of a network of client, coach, and server devices in accordance with some embodiments.

Numerous details are described herein in order to provide a thorough understanding of the example embodiments illustrated in the accompanying drawings. However, some embodiments may be practiced without many of the specific details, and the scope of the claims is only limited by those features and aspects specifically recited in the claims. Furthermore, some processes, components, and materials have not been described in exhaustive detail so as not to unnecessarily obscure pertinent aspects of the embodiments described herein.

The collaboration concepts described herein use real-time, bidirectional, and event-based communication protocols to enable communication between users and experts while working on the same financial picture, series of steps, or other iterative collaborative decision tools.

The application of embodiments of this technology has benefits that differ from anything used in the industry. For instance, real time changes can be made between users and experts. Further, information can be exchanged bi-directionally—instead of merely seeing the same screen, bi-directional information exchange allows for experts and/or users to have different interfaces/UI, functionality, and levels of control, while still working on the same underlying financial picture or other decision support tools (vs. merely co-browsing, which requires the expert to "browse with" users simultaneously on the user's interface, one screen at a time). Further, event-based features drive the collaboration. The expert and the user's interfaces are "listening" for changes, and either the expert and/or the user can "push" a change or multiple changes to the other, which includes running a command on the respective expert and/or user device. Examples may include changing a variable on a user's financial picture, taking the user to a new view, adding a step for the user to complete, or adding an action in a financial decision making tool. This level of control allows the expert and/or the user to queue changes before explicitly pushing them to the other party at a point where it makes sense in the discussion.

The concepts discussed above are implemented, for example, in persistent digital environments referred to herein as "rooms" or "workspaces." Rooms enable iterative collaboration across multiple use cases. For example, rooms are collaborative areas where both users and experts can enter to collaborate on an individual user's financial picture or other decision making collaboration tool. This type of collaboration enables multiple modes of decision support to be completed while maintaining personalized visualizations of trade-offs for each user, and enabling each application of the use case to design the optimal user experience for the expert.

Example implementations include: (i) one user collaborating with one expert in real time, (ii) one user collaborating with multiple experts in real time, (iii) multiple users collaborating with one expert in real time, and (iv) multiple users collaborating with multiple experts in real time. In each of the aforementioned implementations, the collaboration may be asynchronous (described in more detail below).

FIG. 1 depicts an example system 100 for enabling real-time iterative collaborative decision support. In some implementations, one or more client devices 102 interact with one or more coach devices 104 and a server 122. In some implementations, each component is communicatively coupled by one or more communication networks 110 (e.g., the Internet).

Client devices 102 are for use by clients (also referred to herein as users or consumers), and coach devices 104 are for use by coaches (also referred to herein as advisors or experts). In some implementations, the client devices 102 and coach devices 104 are computing devices (e.g., personal computers, laptops, mobile devices, and so forth) enabling communication through the network(s) 110. The client and coach devices run instantiations of a web application referred to herein as the "Collaborator" web application. The Collaborator web applications have client or coach specific capabilities described in more detail below with regard to FIGS. 2 and 3. The server 122, together with data storage device 124, runs an applications referred to herein as the "Coordinator" application. The server 122 and storage 124 are sometimes collectively referred to herein as "coordinator 120."

Client devices 102 are typically electronic devices, including one or more of a desktop or laptop computer (such as client 102-1), a smart phone or any other type of electronic mobile device (such as client 102-2), smart speaker, or any other type of electronic computing device not yet developed as of the filing date of this document.

Coach devices 104 are typically electronic devices, including one or more of a desktop or laptop computer. Optionally, a coach device 104 may be a smart phone or any other type of electronic mobile device, or any other type of electronic computing device not yet developed as of the filing date of this document.

Communication network(s) 110 optionally communicate via wired and/or wireless communication connections. Communication networks optionally communicate with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication. Wireless communication connections optionally use any of a plurality of communications standards, protocols and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11ac, IEEE 802.11ax, IEEE 802.11b, IEEE 802.11g and/or IEEE 802.11n), voice over Internet Protocol (VoIP), Wi-MAX, and/or any other suitable communication protocol, including communication protocols not yet developed as of the filing date of this document.

Figure 2:
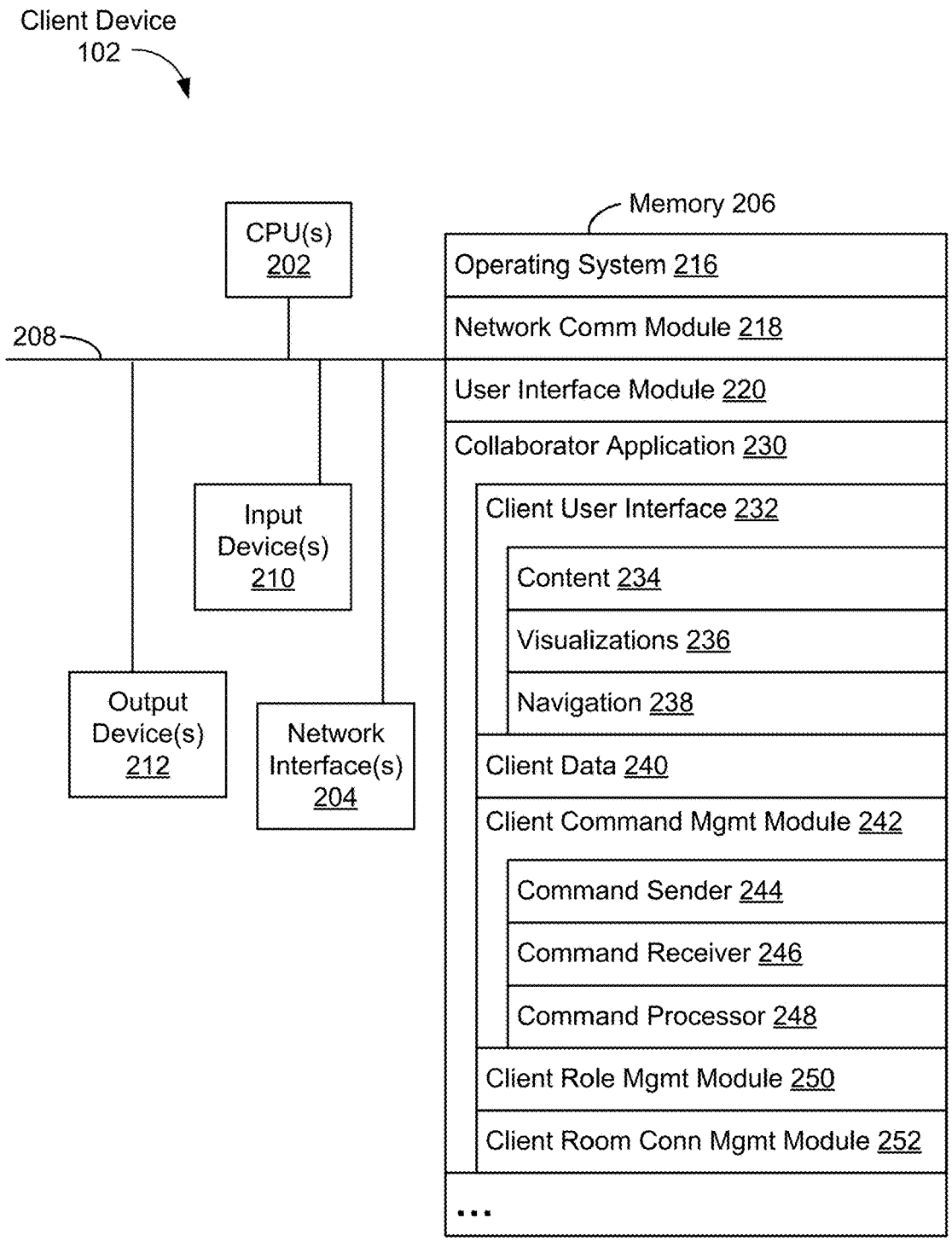
FIG. 2 is a block diagram of a client device in accordance with some embodiments.

FIG. 2 is a block diagram of an example client device 102 in accordance with some embodiments. The client device 102 includes one or more processing units (CPUs) 202, one or more network interfaces 204, memory 206, and one or more communication buses 208 for interconnecting these components (sometimes called a chipset). In some embodiments, the client device 102 includes one or more input devices 210 that facilitate user input, such as a keyboard, a mouse, a voice-command input unit or microphone, a touch screen display, a touch-sensitive input pad, a gesture capturing camera, or other input buttons or controls. In some embodiments, the client device 102 includes one or more output devices 212 that enable presentation of user interfaces and display content, including one or more speakers and/or one or more visual displays.

Memory 206 may include high-speed random access memory, such as DRAM, SRAM, DDR RAM, or other random access solid state memory devices, and optionally may include non-volatile memory, such as one or more magnetic disk storage devices, one or more optical disk storage devices, one or more flash memory devices, or one or more other non-volatile solid state storage devices. Memory 206, optionally, includes one or more storage devices remotely located from one or more processing units 202. Memory 206, or alternatively the non-volatile memory within memory 206, includes a non-transitory computer readable storage medium. In some implementations, memory 206, or the non-transitory computer readable storage medium of memory 206, stores the following programs, modules, and data structures, or a subset or superset thereof:

- Operating system 216 including procedures for handling various basic system services and for performing hardware dependent tasks;
- Network communication module 218 for connecting the client device 102 to other devices (e.g., one or more coach devices 104 and server 122) via one or more network interfaces 204 (wired or wireless) and one or more networks 110, such as the Internet, other wide area networks, local area networks, metropolitan area networks, and so on;
- User interface module 220 for enabling presentation of information (e.g., a graphical user interface for presenting applications, widgets, websites and web pages thereof, and/or games, audio and/or video content, text, etc.) at the client device 102 via one or more output devices 212 (e.g., displays, speakers, etc.); and
- Collaborator application 230, for executing the following operations and processing data using a web browser implemented at the client device 102, or using any other application executed on the operating system 216 of the client device 102, including:
    - Client user interface 232, for displaying content 234 (e.g., data 1204 in FIG. 12), visualizations 236 (e.g., chart 1202 in FIG. 12), and navigation elements 238 as described below with reference to FIGS. 5-13;
    - Client data 240, for storing a local copy of data furnished by a client using the client device 102 (e.g., data 1204 in FIG. 12);
    - Client command management module 242, including command sender 244 for sending client-initiated commands to a coach or to a server through network(s) 110, command receiver 246 for receiving coach-initiated commands from a coach or from a server through network(s) 110, and command processor 248 for processing commands received by the command receiver 246;
    - Client role management module 250 for managing the role of the client using the client device 102; and
    - Client room connection management module 252 for managing the connection between the client device 102, one or more coach devices 104, and/or a server 122.

Each of the above identified elements may be stored in one or more of the previously mentioned memory devices, and corresponds to a set of instructions for performing a function described above. The above identified modules or programs (i.e., sets of instructions) need not be implemented as separate software programs, procedures, modules or data structures, and thus various subsets of these modules may be combined or otherwise re-arranged in various implementations. In some implementations, memory 206, optionally, stores a subset of the modules and data structures identified above. Furthermore, memory 206, optionally, stores additional modules and data structures not described above.

Figure 3:
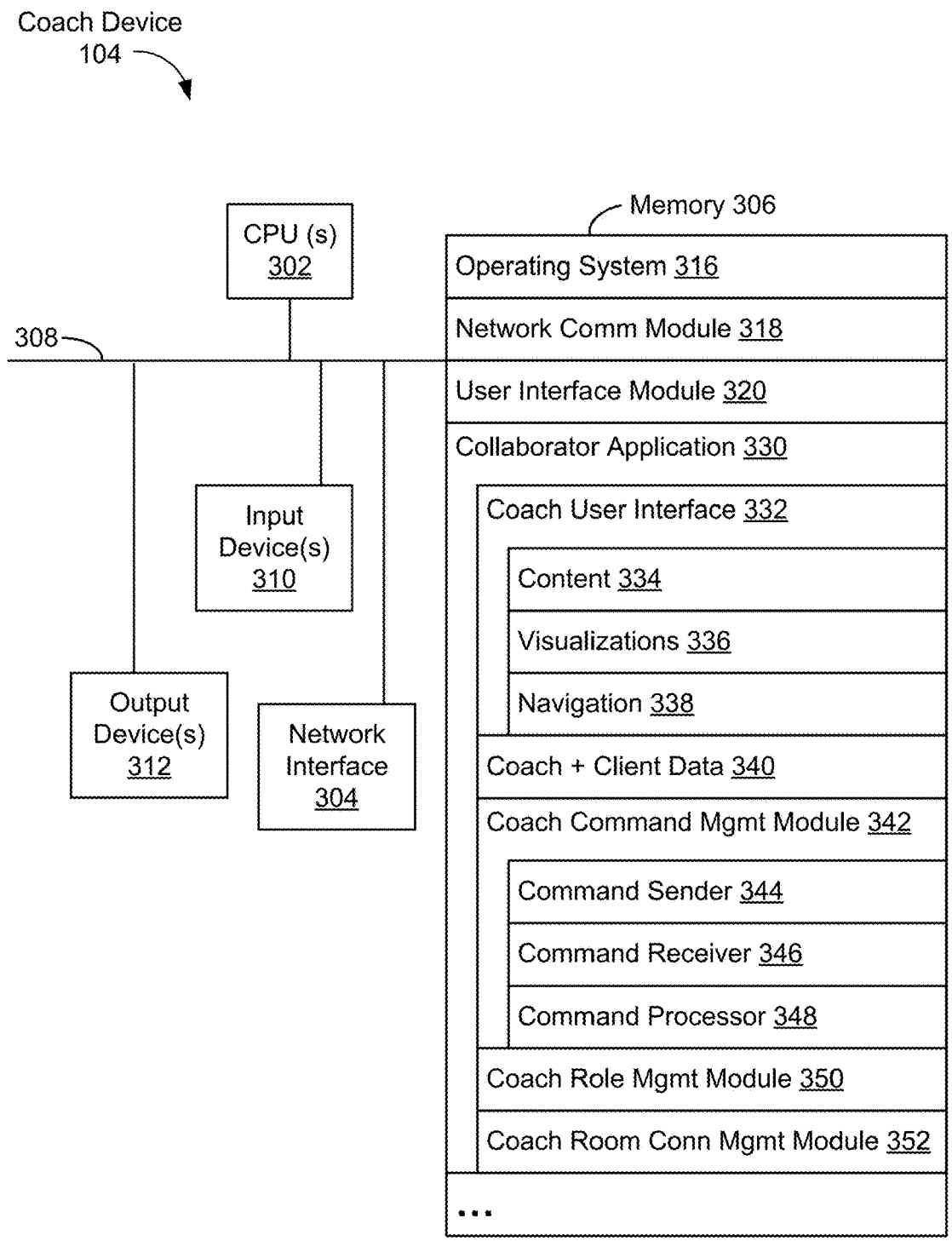
FIG. 3 is a block diagram of a coach device in accordance with some embodiments.

FIG. 3 is a block diagram of an example coach device 104 in accordance with some embodiments. The coach device 104 includes one or more processing units (CPUs) 302, one or more network interfaces 304, memory 306, and one or more communication buses 308 for interconnecting these components (sometimes called a chipset). In some embodiments, the coach device 104 includes one or more input devices 310 that facilitate user input, such as a keyboard, a mouse, a voice-command input unit or microphone, a touch screen display, a touch-sensitive input pad, a gesture capturing camera, or other input buttons or controls. In some embodiments, the coach device 104 includes one or more output devices 312 that enable presentation of user interfaces and display content, including one or more speakers and/or one or more visual displays.

Memory 306 may include high-speed random access memory, such as DRAM, SRAM, DDR RAM, or other random access solid state memory devices, and optionally may include non-volatile memory, such as one or more magnetic disk storage devices, one or more optical disk storage devices, one or more flash memory devices, or one or more other non-volatile solid state storage devices. Memory 306, optionally, includes one or more storage devices remotely located from one or more processing units 302. Memory 306, or alternatively the non-volatile memory within memory 306, includes a non-transitory computer readable storage medium. In some implementations, memory 306, or the non-transitory computer readable storage medium of memory 306, stores the following programs, modules, and data structures, or a subset or superset thereof:

- Operating system 316 including procedures for handling various basic system services and for performing hardware dependent tasks;
- Network communication module 318 for connecting the coach device 104 to other devices (e.g., one or more client devices 102 and server 122) via one or more network interfaces 304 (wired or wireless) and one or more networks 110, such as the Internet, other wide area networks, local area networks, metropolitan area networks, and so on;
- User interface module 320 for enabling presentation of information (e.g., a graphical user interface for presenting applications, widgets, websites and web pages thereof, and/or games, audio and/or video content, text, etc.) at the coach device 104 via one or more output devices 312 (e.g., displays, speakers, etc.); and
- Collaborator application 330, for executing the following operations and processing data using a web browser implemented at the coach device 104, or using any other application executed on the operating system 316 of the coach device 104, including:
  - Coach user interface 332, for displaying content 334 (e.g., data 1204 in FIG. 12), visualizations 336 (e.g., chart 1202 in FIG. 12), and navigation elements 338 as described below with reference to FIGS. 5-13;
  - Coach and client data 340, for storing a local copy of data furnished by a coach using the coach device 104 (e.g., data 1204 in FIG. 12), and/or data furnished by one or more clients using one or more client devices 102 (if the coach device 104 is communicatively coupled to a client device 102);
  - Coach command management module 342, including command sender 344 for sending coach-initiated commands to a client or to a server through network(s) 110, command receiver 346 for receiving client-initiated commands from a client or from a server through network(s) 110, and command processor 348 for processing commands received by the command receiver 346;
  - Coach role management module 350 for managing the role of the coach using the coach device 104; and
  - Coach room connection management module 352 for managing the connection between the coach device 104, one or more client devices 102, and/or a server 122.

Each of the above identified elements may be stored in one or more of the previously mentioned memory devices, and corresponds to a set of instructions for performing a function described above. The above identified modules or programs (i.e., sets of instructions) need not be implemented as separate software programs, procedures, modules or data structures, and thus various subsets of these modules may be combined or otherwise re-arranged in various implementations. In some implementations, memory 306, optionally, stores a subset of the modules and data structures identified above. Furthermore, memory 306, optionally, stores additional modules and data structures not described above.

Figure 4:
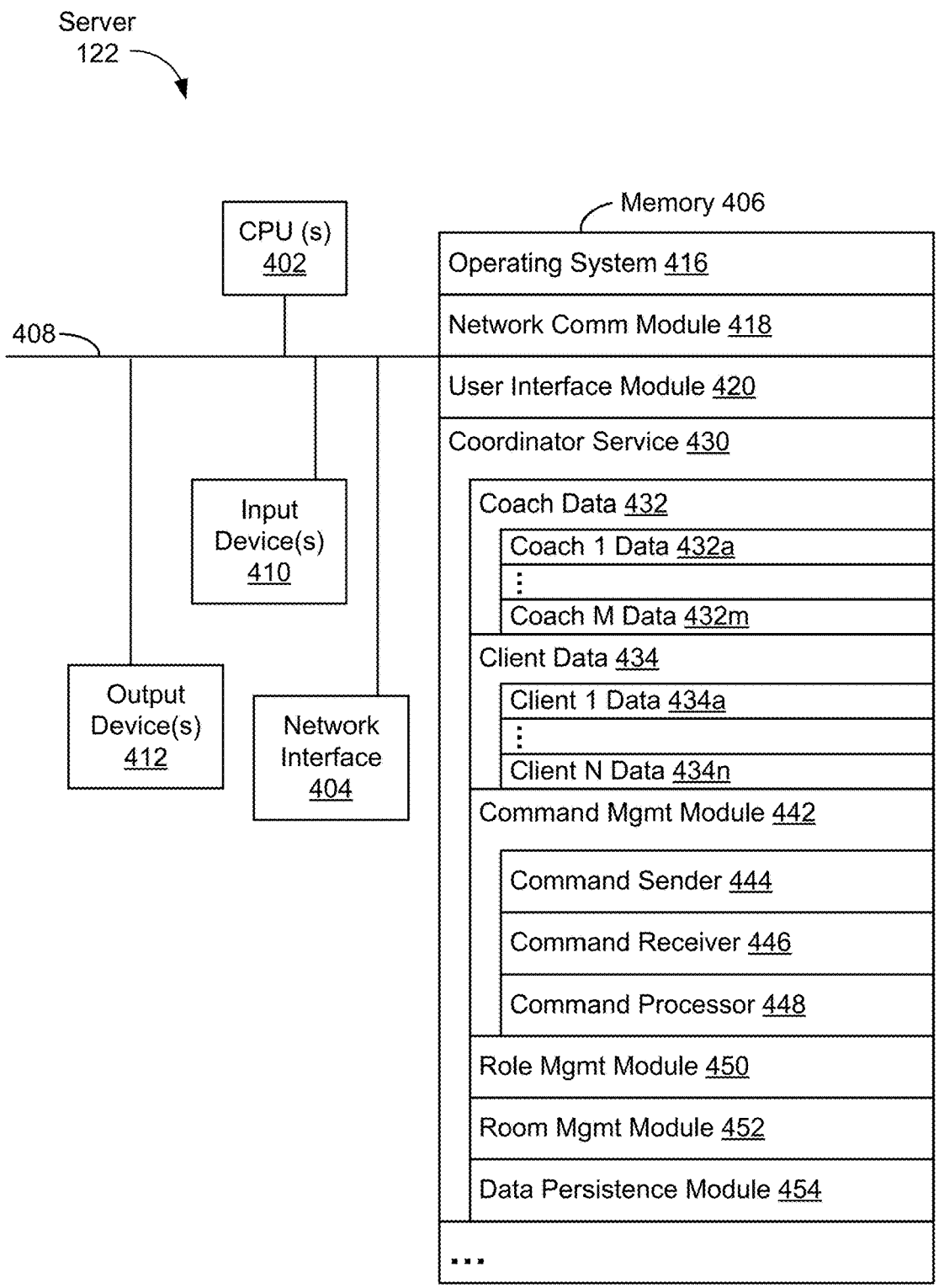
FIG. 4 is a block diagram of a server device in accordance with some embodiments.

FIG. 4 is a block diagram of an example server 122 in accordance with some embodiments. The server 122 includes one or more processing units (CPUs) 402, one or more network interfaces 404, memory 406, and one or more communication buses 408 for interconnecting these components (sometimes called a chipset). In some embodiments, the server 122 includes one or more input devices 410 that facilitate user input, such as a keyboard, a mouse, a voice-command input unit or microphone, a touch screen display, a touch-sensitive input pad, a gesture capturing camera, or other input buttons or controls. In some embodiments, the server 122 includes one or more output devices 412 that enable presentation of user interfaces and display content, including one or more speakers and/or one or more visual displays.

Memory 406 may include high-speed random access memory, such as DRAM, SRAM, DDR RAM, or other random access solid state memory devices, and optionally may include non-volatile memory, such as one or more magnetic disk storage devices, one or more optical disk storage devices, one or more flash memory devices, or one or more other non-volatile solid state storage devices. Memory 406, optionally, includes one or more storage devices remotely located from one or more processing units 402. Memory 406, or alternatively the non-volatile memory within memory 406, includes a non-transitory computer readable storage medium. In some implementations, memory 406, or the non-transitory computer readable storage medium of memory 406, stores the following programs, modules, and data structures, or a subset or superset thereof:

- Operating system 416 including procedures for handling various basic system services and for performing hardware dependent tasks;
- Network communication module 418 for connecting the server 122 to other devices (e.g., one or more client devices 102 and one or more coach devices 104) via one or more network interfaces 404 (wired or wireless) and one or more networks 110, such as the Internet, other wide area networks, local area networks, metropolitan area networks, and so on;
- User interface module 420 for enabling presentation of information (e.g., a graphical user interface for presenting applications, widgets, websites and web pages thereof, and/or games, audio and/or video content, text, etc.) at the server 122 via one or more output devices 412 (e.g., displays, speakers, etc.); and
- Coordinator service 430, for executing the following operations and processing data associated with one or more client devices 102 and coach devices 104, including:
  - Coach data 432, for storing copies of data associated with a plurality of coach devices 104 (e.g., data associated with M coach devices, where M is an integer greater than or equal to 1);
  - Client data 434, for storing copies of data associated with a plurality of client devices 102 (e.g., data associated with N client devices, where N is an integer greater than or equal to 1);
  - Command management module 442, including command sender 444 for sending commands to client and coach devices, command receiver 446 for receiving commands from client and coach devices, and command processor 448 for processing commands received by client and coach devices;
  - Role management module 450 for managing the role of client and coach devices with regard to respective rooms;
  - Room management module 452 for managing the connection between one or more client devices 102, one or more coach devices 104, and the server 122; and Data persistence module 454 for managing storage of client and coach data after a room associated with the client and coach data is terminated.

Each of the above identified elements may be stored in one or more of the previously mentioned memory devices, and corresponds to a set of instructions for performing a function described above. The above identified modules or programs (i.e., sets of instructions) need not be implemented as separate software programs, procedures, modules or data structures, and thus various subsets of these modules may be combined or otherwise re-arranged in various implementations. In some implementations, memory 406, optionally, stores a subset of the modules and data structures identified above. Furthermore, memory 406, optionally, stores additional modules and data structures not described above.

Event-Driven Communication

Figure 5:
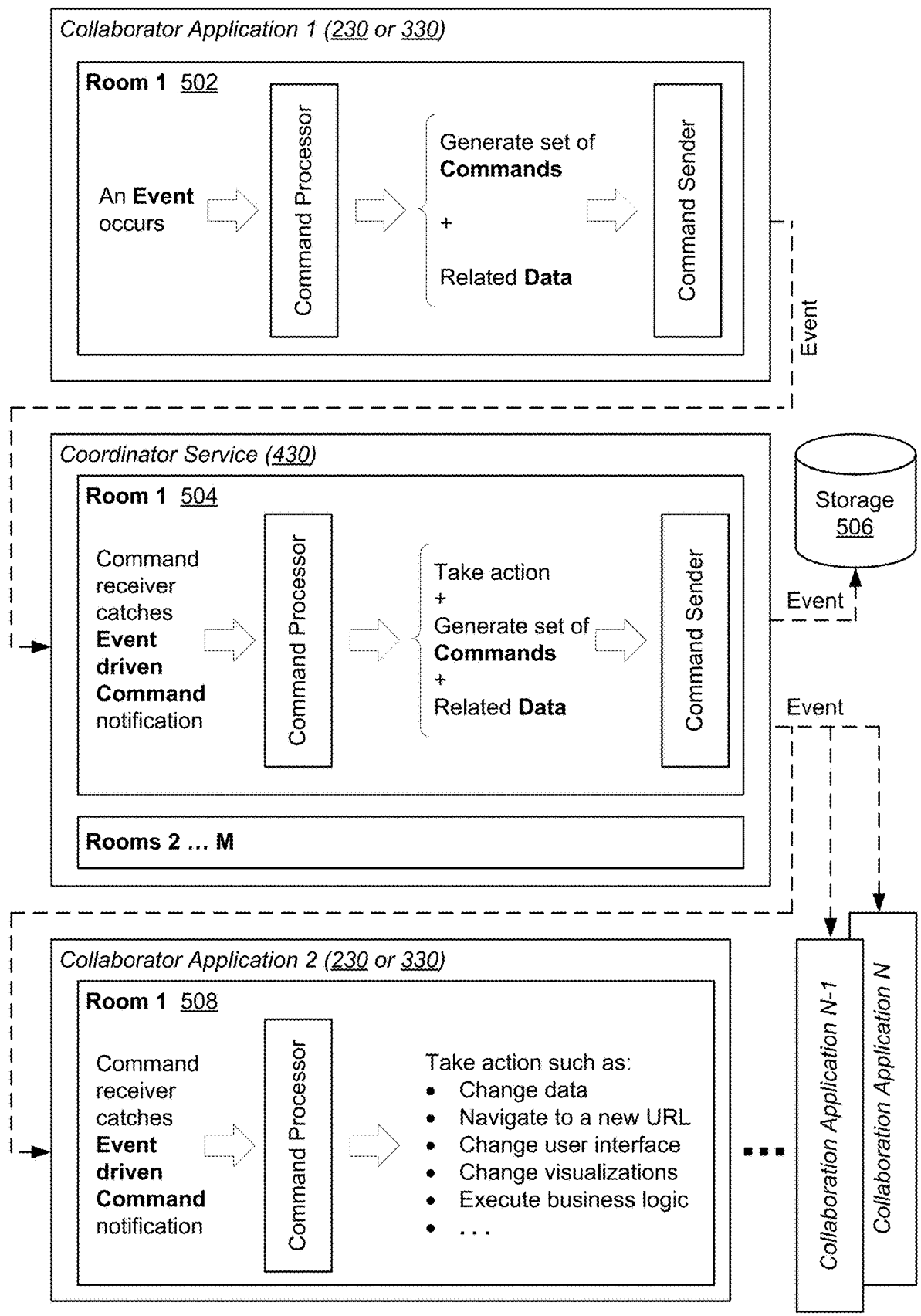
FIG. 5 illustrates an example data flow diagram in accordance with some embodiments.

FIG. 5 illustrates an example data flow diagram in accordance with some embodiments. The data flow enables event-driven communication among (i) one or more client collaborator applications 230 at a client device 102, and/or (ii) one or more coach collaborator applications 330 at a coach device 104. The collaborator applications leverage a coordinator service 430 at a server 122. In some embodiments, N collaborator applications may leverage the coordinator service 430, where N is an integer greater than or equal to 1.

The example embodiment illustrated in FIG. 5 depicts a collaboration between two or more collaborators (devices running a collaborator application) using the same room (Room 1). The dashed lines represent real time event notifications. Real time event notifications are notifications which are sent and received in real time, or near real time, by client devices 102 and coach devices 104 via the server 122 during a particular collaboration. While the example describes use of one room, the coordinator service 430 may support parallel collaborations in M rooms, where M is an integer greater than or equal to 1.

The first collaborator application executes a workspace 502 referred to as Room 1. At Room 1, an event occurs. The event is triggered by a client or coach taking an action at a client or coach device. The action may be inspired by anything of interest to the client or coach in the context of the collaborator application (described in more detail below). The event is caught by a command processor which translates the event into a set of commands and related data objects. A command sender then uses the commands and related data to issue an event notification. The event notification includes the set of commands and related data, and is issued for the specific room (Room 1 in this case) to the coordinator service 430 at server 122.

The coordinator service 430 catches the event driven command notification in a workspace 504 also referred to as Room 1 due to its use as part of the collaboration with the first collaborator application. At Room 1 (504), a command processor takes one or more actions by executing some commands locally, while generating another set of commands and related data object tuples to be transmitted by a command sender as an event driven command notification to other collaboration applications (2 through N) for execution.

At least a portion of the data in the command and data object tuples is stored in data storage 506 (corresponding to coach data 432 and client data 434 in memory 406 of the server 122).

A second collaboration application (230 or 330) catches the event driven command notification in a workspace 508 also referred to as Room 1 due to its use as part of the collaboration with the first collaborator application. At Room 1 (508), a command processor executes the commands locally with the related data objects. Executing the commands includes taking one or more actions including, for example, changing data, navigating to a new URL, changing a user interface, changing a visualization, executing business logic, and so forth.

FIGS. 6, 7A-7C, 8, 9A-9C, 10A-10B, and 11A-11B are flow diagrams of connection setup processes or interactions in accordance with some embodiments. The processes may be performed at one or more client devices 102, each having one or more processors 202 and memory 206 storing one or more programs (e.g., collaborator application 230) for execution by the one or more processors; one or more coach devices 104, each having one or more processors 302 and memory 306 storing one or more programs (e.g., collaborator application 330) for execution by the one or more processors; and one or more servers 122, each having one or more processors 402 and memory 406 storing one or more programs (e.g., coordinator service 430) for execution by the one or more processors. In some implementations, respective non-transitory computer readable storage media store one or more respective programs, the one or more respective programs including instructions, which, when executed by the client device(s) 102, the coach device(s) 104, and the server(s) 122, with one or more respective processors, cause the electronic client device(s) 102, the coach device(s) 104, and the server(s) 122 to perform the respective processes in the respective figures. Additionally, the order of the operations described with reference to FIGS. 6-11B is optional. Some operations may be reordered, while others may be left out.

One Client, One Coach

Figure 6:
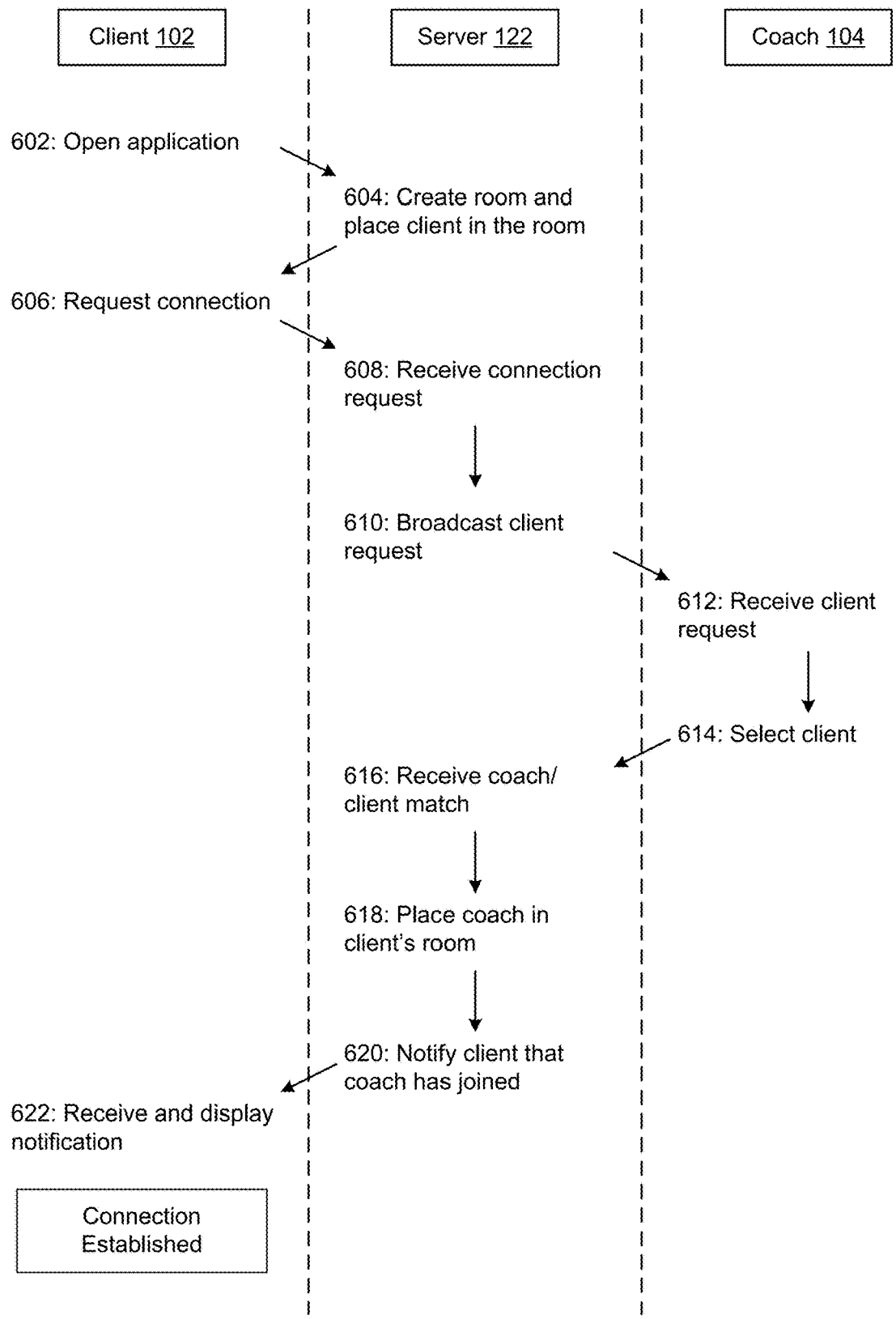
FIG. 6 is a flow diagram of a connection setup for one client and one coach in accordance with some embodiments.

FIG. 6 is a flow diagram of a connection setup process 600 for one client and one coach in accordance with some embodiments. A client, using a client device 102, opens (602) the collaborator application 230. Upon opening, the collaborator application 230 (e.g., client room connection management module 252) notifies the server 122, which results in the server (e.g., room management module 452) creating (604) a room and placing the client in the room (e.g., Room 1-502, FIG. 5). The client, using the client device 102, requests (606) to be connected with a coach. The server 122 receives (608) the connection request from the client device 102, and broadcasts (608) availability of the client to one or more coaches (via coach device(s) 104). Stated another way, coaches are notified that a client is awaiting matching. In response to the broadcast of availability of the client device, a particular coach receives (612) the broadcast and selects (412) the client (e.g., using the coach room connection management module 352 on a coach device 104). Stated another way, coaches decide which clients to work with and make their selections accordingly.

The server 122 receives (616) a connection request from the particular coach device 104, and in response, the server places (618) the coach into the room with the client (e.g., Room 1-508, FIG. 5). Stated another way, the server associates the coach connection with the room created in step 604 for the client. The server 122 notifies (620) the client device 102 that the coach has joined the room, and the client receives and displays (622) the notification. At this point, a connection has been established between a client device 102 and a coach device 104 through the server 122, allowing a client and a coach to collaborate (e.g., enter data, issue commands, navigate, and so forth).

Figure 7A:
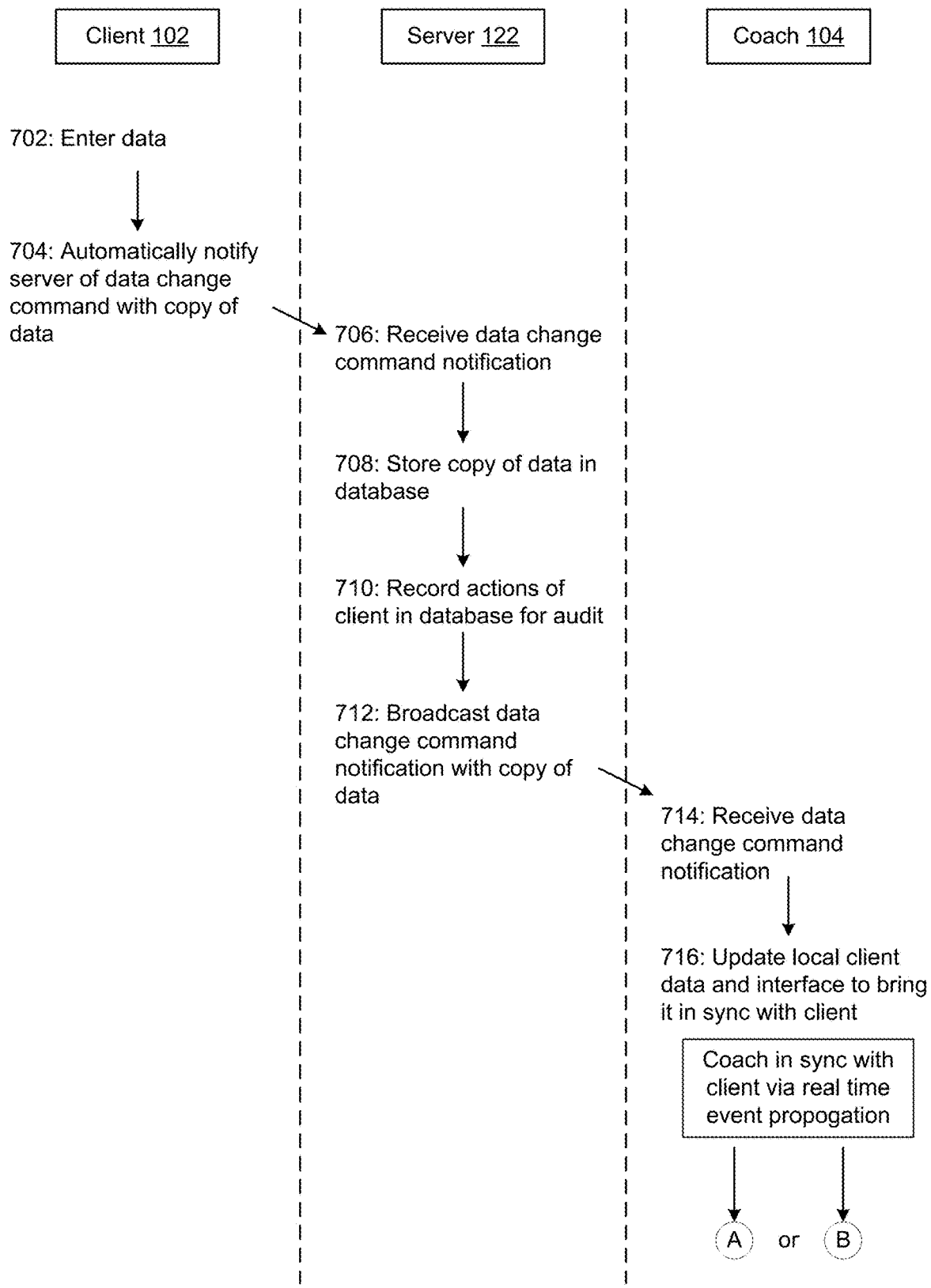
FIGS. 7A-7C are flow diagrams of an interaction between one client and one coach in accordance with some embodiments.
Figure 7B:
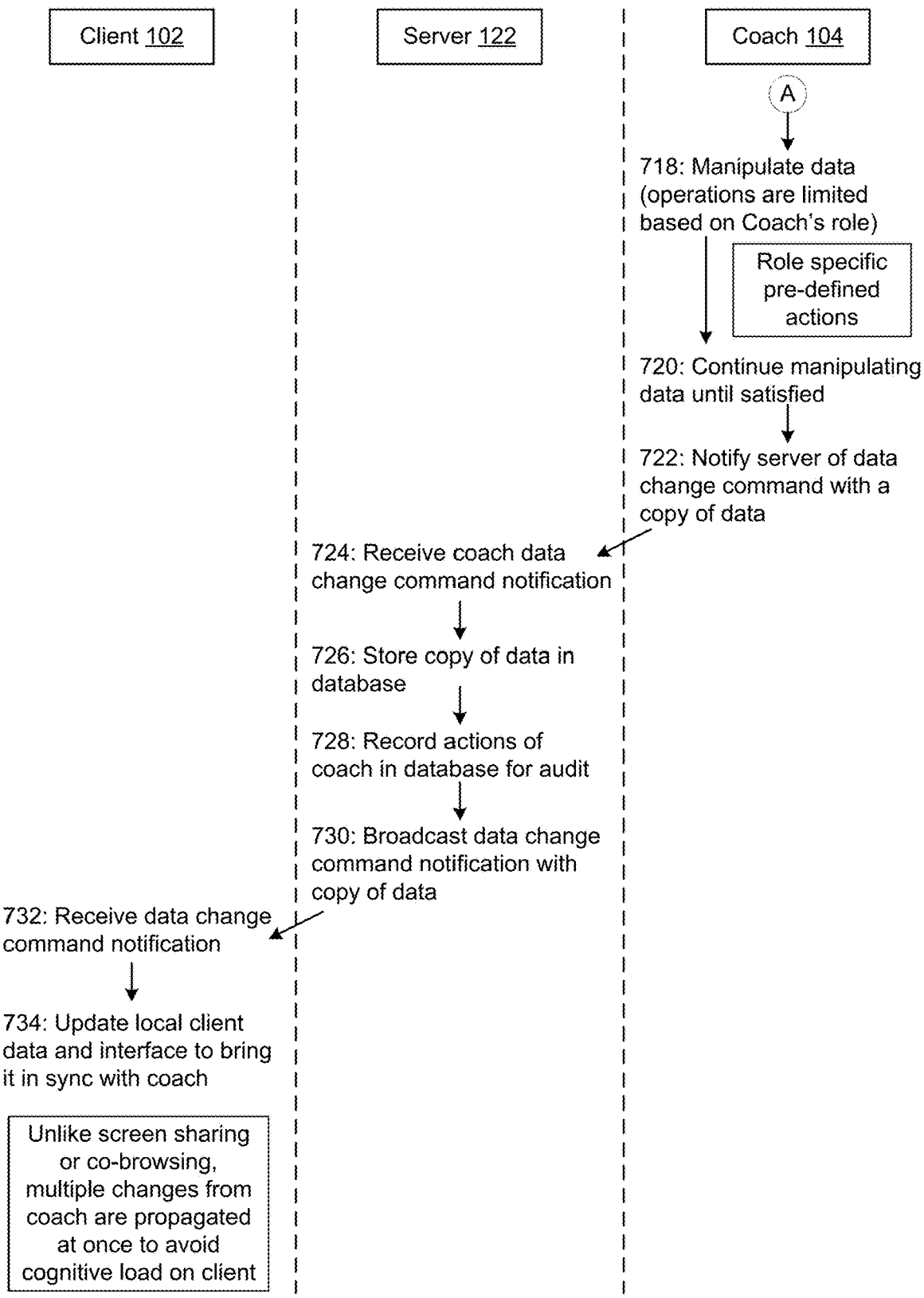
Figure 7C:
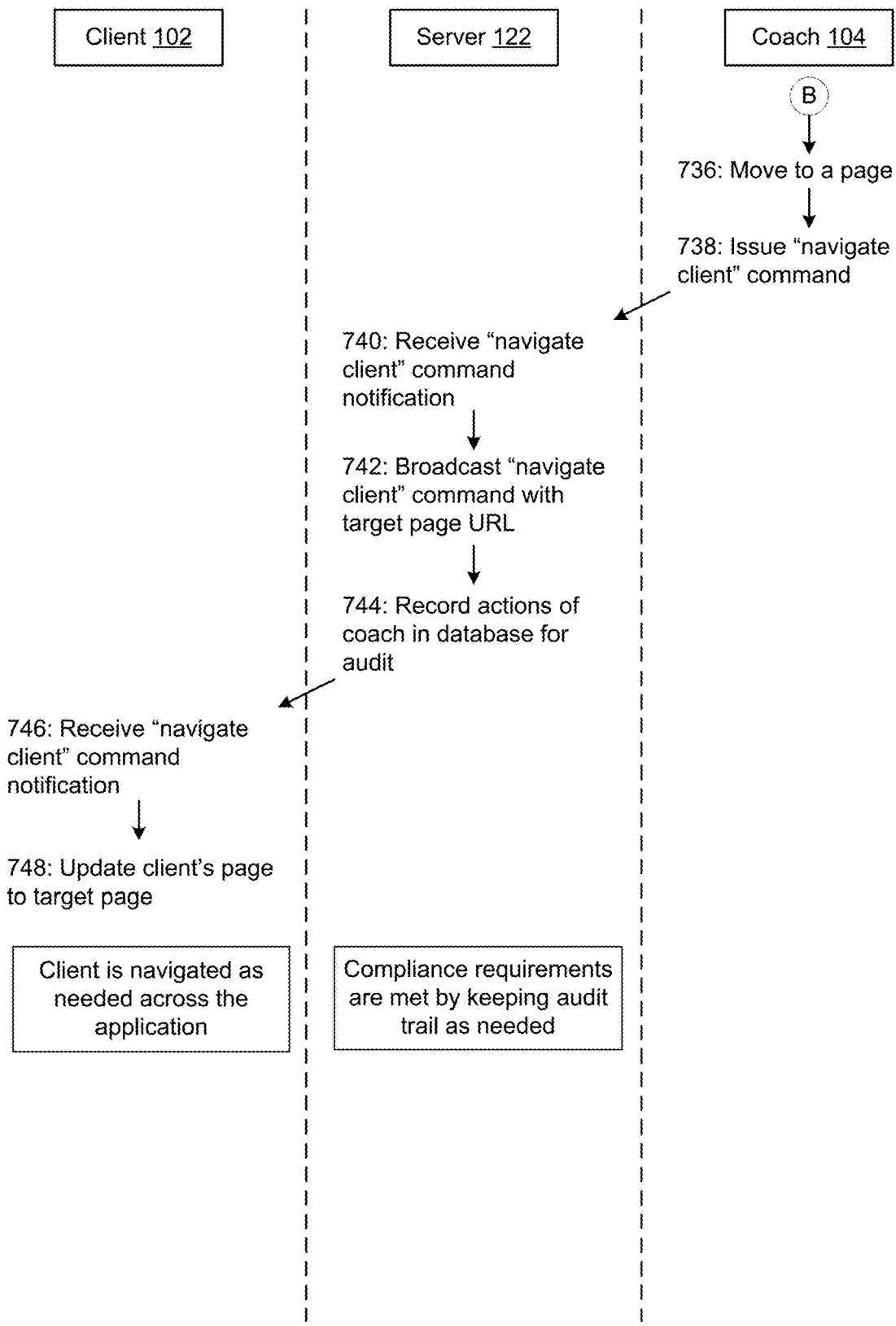

FIGS. 7A-7C are flow diagrams of an interaction process 700 between one client and one coach in accordance with some embodiments. The client enters data (702), such as profile information, financial data, retirement goals, and so forth, using the client user interface 232. Examples of financial data may include data correlating to and/or impacting the client's financial data, such as: (i) healthcare data (e.g., to calculate expenses and make tradeoffs on health decisions), (ii) risk and/or behavioral data that impacts probability and/or cost of future events (e.g., driving performance, house fact/factors, longevity factors, and so forth, that would be used in determining tradeoffs around risk and/or associated future financial impacts, both to insurance costs and costs related to a probabilistic event), and/or (iii) commercial and/or operational data (e.g., including applications in commercial insurance, such as telematics data about a client's fleet, and so forth).

The client enters the data using the client user interface (UI) 232 at the client device. For example, the system populates the client's UI with content 234 and/or visualizations 236 representing the collaborator application's prompts for data and/or a coach's requests for data and provides appropriate fields in the client UI in which the client may enter the requested data. The client device automatically notifies (704) the server of the data change by sending a data change command (via command sender 244) which includes the data entered by the client. The server receives (706) the data change command notification (via command receiver 446) and stores (708) the data in a database (e.g., client 1 data 434*a*). In addition to the client's data, the server also records (710) actions of the client in the database to preserve for later audits. The server broadcasts (712) the data change command notification including the data (via command sender 444), and the coach device receives (714) the data change command notification (via command receiver 346). Upon receiving the command, the coach device updates (716) local client data corresponding to the client (client data 340) to synchronize the coach device's copy of the data with the client's and server's copy of the data. At this point, the coach device is synchronized with the client device via, for example, real time event propagation. In some embodiments, each time the client enters data, the server updates the coach device in real time (or near real time). Stated another way, the coach device displays the client's data (via coach UI 332) in real time (or near real time) to the coach as the client enters or otherwise submits the data so that the coach can act on the data in an efficient manner during the coach's collaboration with the client. In some implementations, the client's data itself is not displayed on the coach UI; rather, the coach collaborator application 330 displays another form of the data such as visualizations 336 (e.g., graphs or charts) or secondary data related to the client data (e.g., financial projections) on the coach UI.

At any time during the interaction between the client and the coach, the coach may manipulate (718) the client's data (e.g., by editing the data, adding to the data, performing calculations or projections on the data, and so forth) or enters new data (e.g., results of calculations or projections, explanations, and so forth). For example, the coach uses the client's salary as a basis for financial projections, retirement decision explanations, and so forth. In some embodiments, the ability to manipulate data in certain ways, or even the ability to access the data, or certain portions of the data, is based on the coach's role (managed by coach role management module 350). For example, if the coach's role provides access to financial data but restricts access to health data, the coach collaborator application 330 may allow the coach to manipulate the client's financial data but not manipulate (or even access) the client's health data. In some embodiments, the data manipulations and other types of actions available to the coach are predefined based on the coach's role. Stated another way, the coach performs one or more role-specific predefined actions.

In some embodiments, the coach may perform actions (e.g., manipulate data, navigate to a new page) based on a predefined, customizable library of data and commands stored on the coach device (e.g., stored in a coach command database 340). One benefit may be the ability for coaches to automate common actions or common data entries which may enhance the speed and scale in which coaches can help clients. Customizable actions or events stored on the coach device, as described herein, can trigger a predefined series of multiple commands (e.g., operations 718, 720). In some embodiments, the role management module 350 of the coach device creates, stores, accesses, and/or modifies role-specific "events" on the coaches device that are translated through the command processor into a corresponding library of specific pre-defined commands and corresponding data. The commands and related data are then sent to the server to be propagated to other devices using the real-time event-based information exchange. This allows each coach device to create a personalized library of specific pre-defined commands and corresponding data that is accessible via the coach's UI and can be customized and configured for each coach device. This pre-define library allows coaches to execute a series of steps by triggering a single "event" in the UI, rather than having to input multiple repetitive data entry steps within the UI to achieve the same effect, which is especially useful for common actions a coach takes on a day-by-day basis. In some embodiments, each coach can configure his or her own library of events which automate common items which are used on a day-to-day basis and can leverage both in real-time connections with client devices or asynchronous engagement. This improves the field of expert-guided decision making by streamlining common multi-step data entry tasks for coaches (e.g. common message, series of steps, etc.) and/or specific predefined commands, giving coaches greater control and making them more efficient.

Returning to FIG. 7B, the coach continues to manipulate (720) or otherwise perform actions and events until the coach is ready for the client to view the results of the coach's manipulations and other actions. At that point, the coach causes the room to be updated at the client device. For example, the coach device, in response to the coach executing a data change command, a synchronize command, an update command, or any type of command which communicates updated data or actions by the coach, transmits (722) a data change notification to the server which includes the data that was changed or the new data. In some embodiments, the coach executes this command by selecting an affordance (or any other kind of UI element), such as an "Update" affordance (e.g., 1352 in FIG. 13B) or a Navigation affordance (e.g., "Savings" 1354*a*, "Income" 1354*b*, or "Expenses" 1354*c* in FIG. 13B) in the coach's UI.

The server receives (724) the coach data change command notification, which may include a plurality of commands, and stores (726) the data corresponding with that command in the database associated with the client (e.g., client 1 data 434*a*). The server also records (728) the coach's actions in the database to preserve for later audits. The server broadcasts (730) the data change command notification with the new or changed data, and the client device receives (732) the data change command notification and updates (734) the local copy of the data and the client UI to bring the client collaborator application 230 in synchronization with the coach collaboration application 330. Stated another way, upon performing a plurality of actions and selecting an "Update" element in the coach UI, the coach device synchronizes the data with corresponding data on the client device via the server so that the updated data associated with each of the plurality of actions is synchronized in one step at the client device. As such, unlike screen sharing or co-browsing, multiple changes from the coach are propagated to the client at once.

By allowing the coach to synchronize multiple actions at once, this enables the coach to manage the display and flow of information to the client at a pace that can mitigate cognitive overload and increase understanding. Cognitive overload typically occurs when coaches take a sequence of actions to arrive at a specific illustration or outcome. Conventional systems can confuse users when coaches attempt to illustrate scenarios or outcomes of the impact of a certain decision that require a series of adjustments to users' data, therefore limiting the ability for coaches to help users understand how multiple factors simultaneously impact a decision. Moreover, since conventional systems either broadcast a display of one device's interface to another (i.e., screen sharing) or enable a joint navigation of an interface across multiple devices (i.e., co-browsing), conventional systems force each action a coach takes to be synchronized with what the user sees, causing potential confusion if a coach needs to take multiple actions in sequence to illustrate a point.

However, the client/coach interactions described herein use event-driven command management techniques, the cadence and timing of which is selectively coordinated by the coach device. The operations described herein use a bi-directional, event-based architecture that manages the creation and propagation of commands at the client level, which allows for the cadence, timing and sequence of commands to be coordinated via the coach device through command management. This command management functionality enables a coach device to control the pace and rate in which data updates and commands are provided to the user, which allows coaches to execute a series of commands and updates of information on the coach device that can be selectively "pushed" to a client device instead of forcefully synchronizing every coach action directly to a client device. This enables coaches to manage the flow of real-time data updates and navigation commands on the client device in a way that can be tailored to optimize for users' understanding and the conversation taking place. This improves the field of expert-guided decision making by allowing experts to have additional control over the rate and level of complexity displayed to users so they can bring the depth of their expertise to decision support in real time without overloading users' ability to absorb and understand the concepts being illustrated to them.

Returning to FIG. 7B, at any time during the interaction between the client and the coach, the coach may navigate the client to a new screen by moving (736) or otherwise navigating to a page (e.g., a UI screen). Upon moving to a page, the coach device issues (738) a command, such as a "navigate client" command, which is transmitted to the server (by command sender 344) as a command notification. In some embodiments, the command notification includes a target page, such as a Uniform Resource Locator (URL) or any other type of pointer identifying a page in a web browser or a screen or menu in a UI. The server receives (740) the "navigate client" command notification and broadcasts (742) the command along with the information necessary to communicate the new page to the client device (e.g., the target page URL). The server also records (744) the navigation action(s) in the database to preserve for later audits. As a result of the recording, compliance requirements are met by keeping an audit trail as needed.

The client device receives (746) the navigation command notification and the target page information and (748) updates the client's page in the client UI based on the target page information (e.g., navigates to the page specified by the target URL). As a result of the page update, the client is navigated as needed across the collaborator application 230.

In one example interaction, the coach device transmits two coach actions to the server, and these actions are both transmitted in response to a single synchronize or update command at the coach device. For example, one of the actions includes data entered by the coach based on the client data (e.g., a financial projection or retirement advice), and updating the room based on the action includes populating the client UI with the data (or secondary data based on the data) entered by the coach. Another of the actions includes a navigation command, initiated at the coach device, pointing to a different client UI (e.g., a client UI which is not being displayed at the time the system receives the navigation command), and updating the room based on the action includes causing the client device to navigate from a current UI (e.g., the UI that is displayed at the time the system receives the navigation command) to the different UI (e.g., the UI specified by the coach at the coach device). When the coach performs a data manipulation and a navigation (e.g., updates a retirement age forecast and navigates to a page showing a chart of the forecast), both the data manipulation and the navigation are not released or otherwise forwarded to the client device until the coach device transmits the update command (e.g., as a result of the coach selecting the update affordance 1352, FIG. 13b). In some embodiments, data manipulations are not forwarded to the client device until the coach selects an update affordance (e.g., 1352 in FIG. 13b), but navigation commands are forwarded to the client device when the coach selects a navigation affordance (e.g., 1354a, 1354b, or 1354c in FIG. 13b). Stated another way, data manipulations may be withheld from the client device until the coach selects the update affordance, but navigation commands may be forwarded to the client device immediately upon the coach selecting a navigation affordance.

Eventually, the client device leaves the room (e.g., when the client logs out of the collaboration application 230 or otherwise ends the connection). The client device sends to the server, and the server receives, a notification to terminate the connection with the client and/or a request to end the collaboration session with the coach. In some embodiments, in response to receiving the request, the server (data persistence module 454) saves the client's data (434a) and the coach's data (432a). Upon saving the data, the server terminates the connection with the client device.

When the client wishes to return to the room, in one implementation, the collaboration application 230 picks up where it left off. For example, in accordance with a determination that the client device requesting a connection is associated with client data 434 which has already been saved in the database, the server accesses the client's data saved during the previous session, establishes a connection with the client device (e.g., including populating the client UI with data received during one or more previous sessions with the client device), and broadcasts availability of the client device to available coach devices as in process 600 (FIG. 6). In response to receiving a client selection (616) from a coach device, the server establishes a connection with the coach device and populates a coach UI at the coach device, wherein the coach UI includes at least one element or set of data saved during the previous collaboration session.

In some embodiments, after operations 734 or 748, the process 700 returns to operation 702 when the client enters additional data. The additional data may be independent of the coach's actions (e.g., the user decides to enter additional financial data while waiting for a coach's reply), or the additional data may be based on the coach's actions (e.g., the user may update previously entered data as a result of the coach's suggestion). In addition, the order of some of the operations described in FIGS. 7A-7C may be changed in some embodiments. For instance, the server may execute one or more of the recording operations 710, 728, and 744 before broadcasting commands associated with the recorded data, or after the client device receives the commands associated with the recorded data. Alternatively, the server may not record actions or data in some embodiments (e.g., depending on data sensitivity or relevance to certain types of audits).

Figure 8:
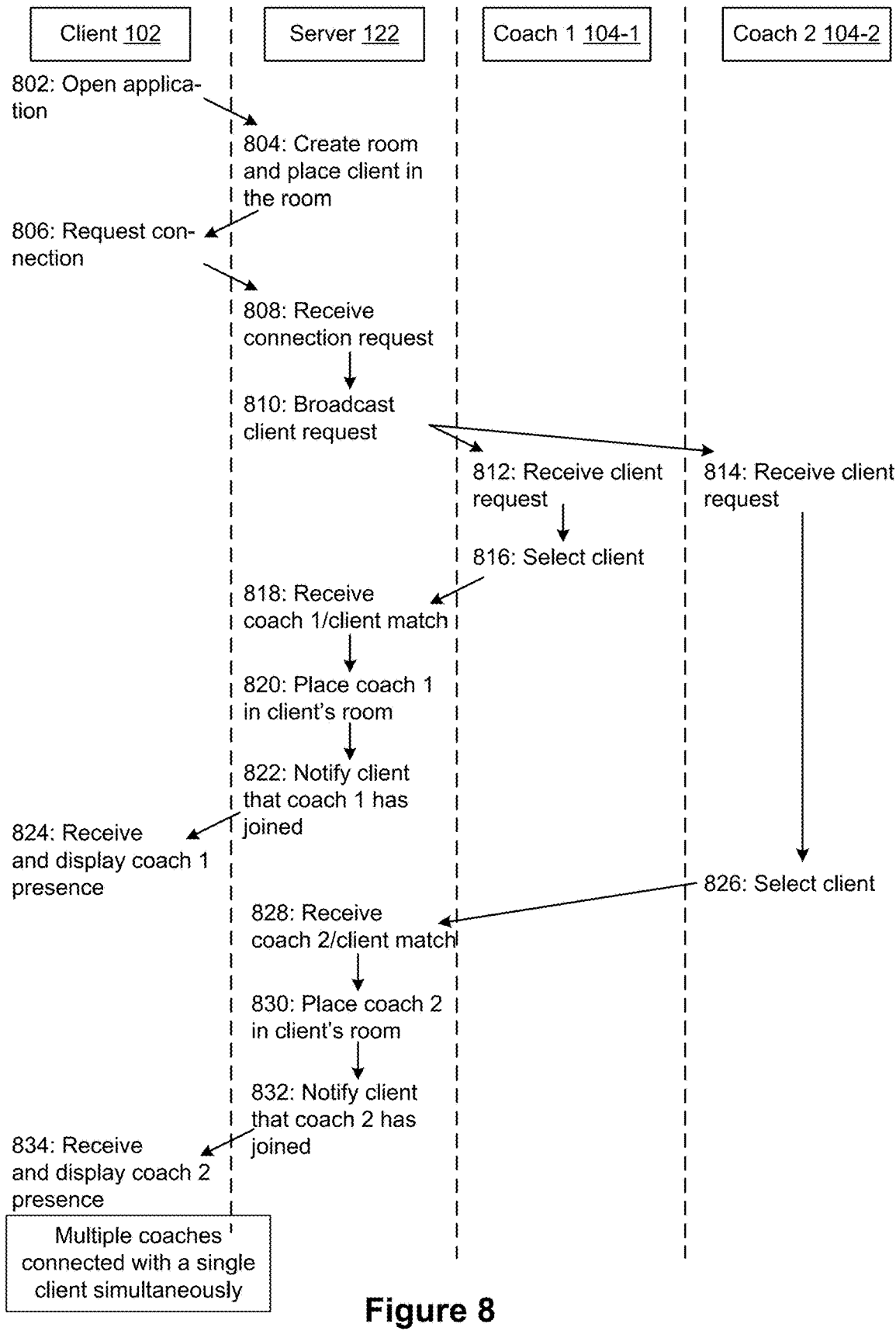
FIG. 8 is a flow diagram of a connection setup for one client and multiple coaches in accordance with some embodiments.
Figure 9A:
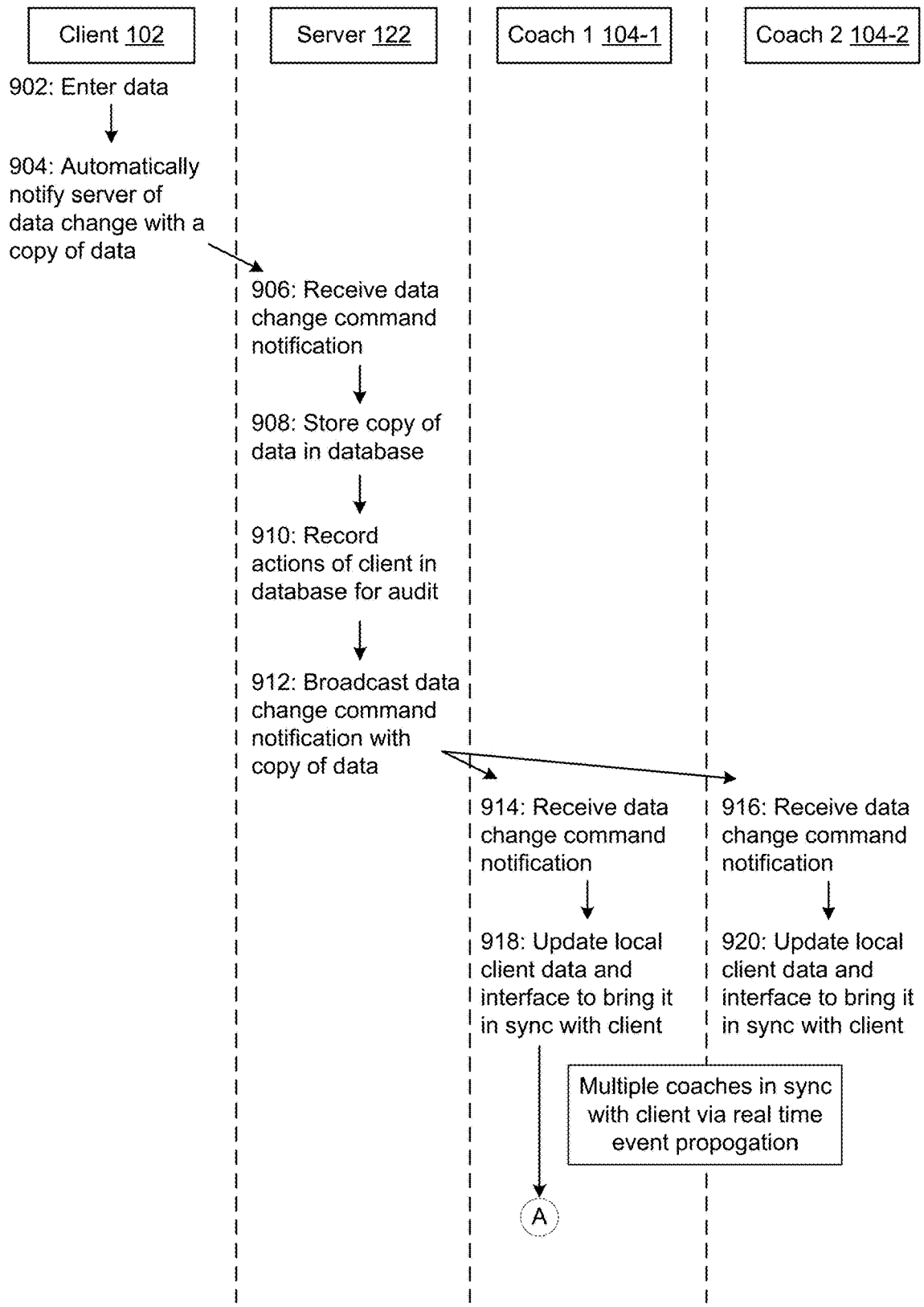
FIGS. 9A-9C are flow diagrams of an interaction between one client and multiple coaches in accordance with some embodiments.
Figure 9B:
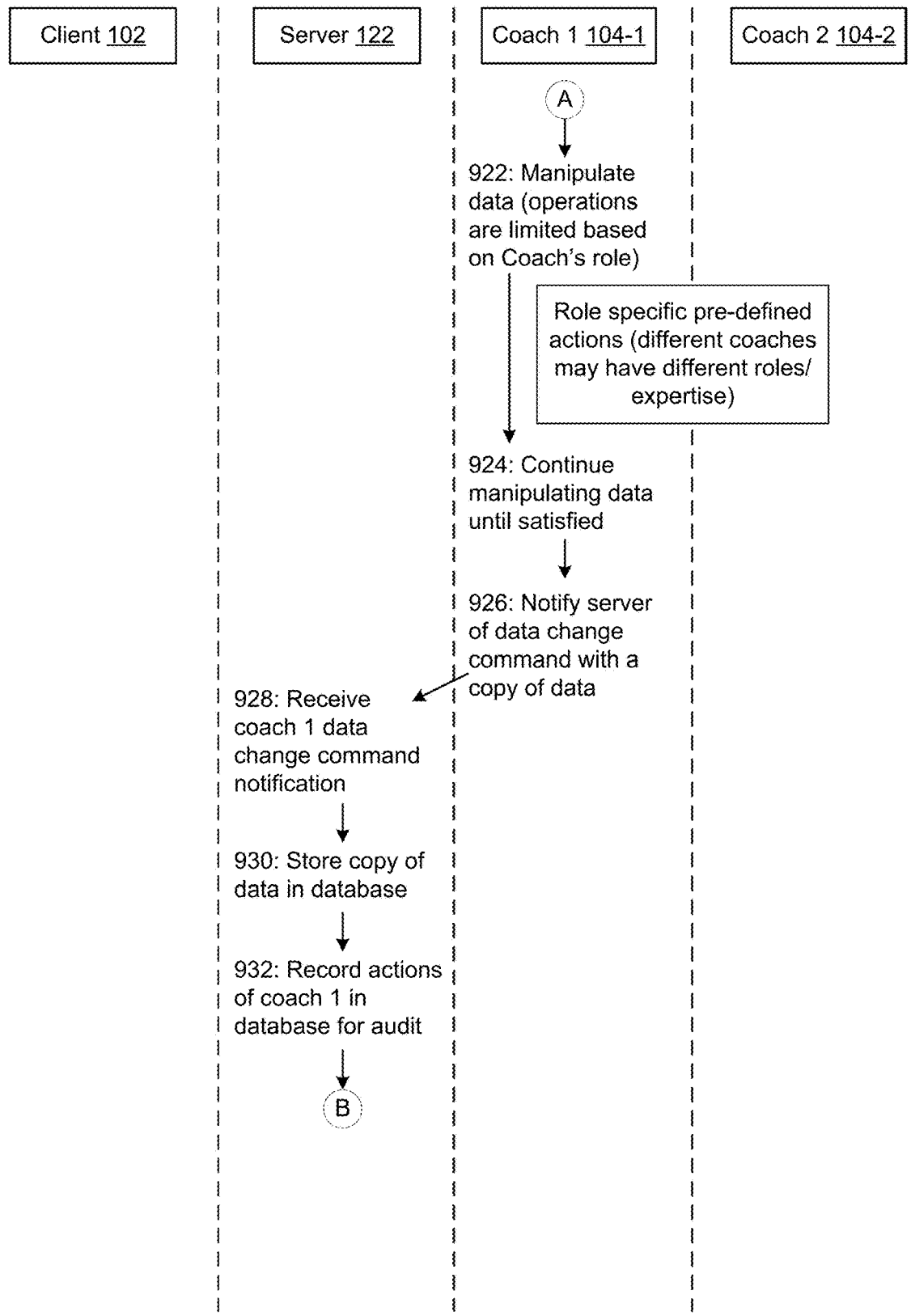
Figure 9C:
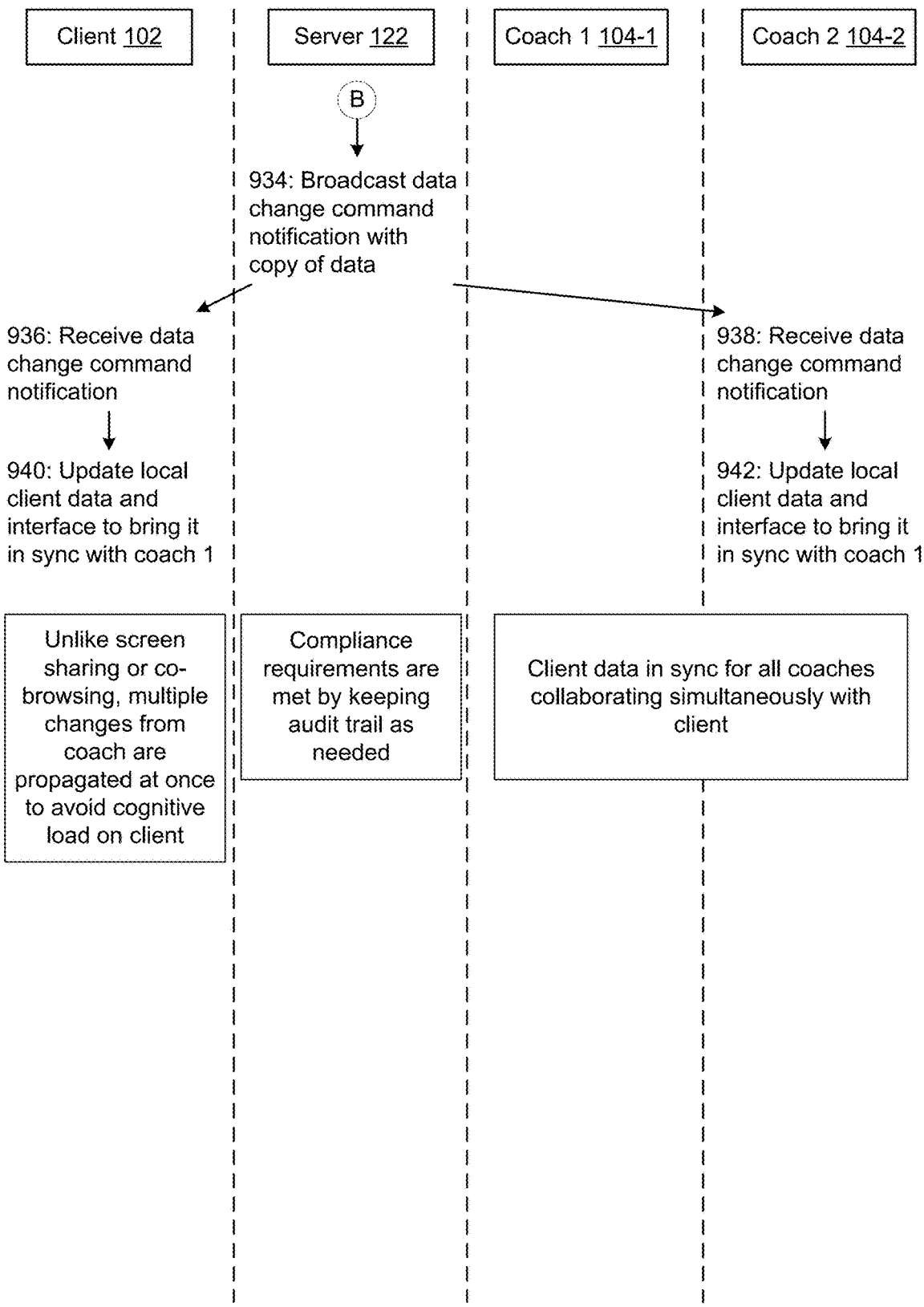

FIGS. 8-9C describe processes for scenarios including one client and multiple coaches, and FIGS. 10A-11B describe processes for scenarios including multiple clients and one coach. Each of these processes include operations similar to those discussed with reference to FIGS. 6-7C above, in addition to new operations. Operations which are similar to those described above may not include the same level of detail with regard to the processes described below for purposes of brevity; however, the details described above should be assumed to apply to the corresponding operations described below unless otherwise specified.

One Client, Multiple Coaches

One benefit of exemplary embodiments, includes the implementation of tools, repository of expertise, and history of client engagement (i.e. data stored in a customer relationship management system) readily available at the point where experts collaborate with clients. This may eliminate a division between the "front-line" customer support associates and specific knowledge experts within an organization. As a result, in some implementations, support staff may persist in the collaborator application and reach out to experts in their organization via the present structure of the application instead of using email or separate systems, to access specific knowledge they may need and collaborate with those experts. In industries where guidance, support, or advice is heavily regulated (e.g. financial services, healthcare, insurance, and so forth) the elimination or reduction of duplicative systems ensures people with the right credentials have access to specific data, thus reducing or eliminating silos across an organization's client/coach collaborator applications and promoting the ability for experts to collaborate in the context of supporting a client. Unlike current solutions that enable a joint navigation of an interface across multiple devices (i.e. co-browsing), some implementations described herein do not lock collaboration between clients and coaches across the same interfaces. This enables, in some embodiments, non-client facing collaboration amongst coaches within the collaborator application, helping to improve the art of customer engagement and internal employee collaboration in a world where regulatory compliance around customer's data privacy is increasingly complex and difficult to manage.

The techniques described herein include integrated role management functionality that conditionally determines which workspaces, data, and commands a device can access with the various collaborator applications. This role management functionality allows different types of user roles (e.g. regulated users, different credentials, etc.) to access, modify, or amend different data that others cannot (e.g. client devices or coaches without credentials) within the context of the collaborator application. One implementation, therefor creates a mechanism in which non-client facing data can be conditionally created, stored, accessed, and modified within the context of the collaborator application. This contextualizes non-client facing collaboration between coaches inside the same application that supports clients, rather than relying on duplicative systems.

Moreover, solutions described herein enable multiple experts (i.e. coaches) to simultaneously view, add, and/or edit non-client facing data provided by other coach devices (e.g. call notes, questions to other experts, suggested approaches, and so forth) and view, add, and/or edit specific client data all within the context of the same application. This facilitates contextually relevant collaboration between experts inside a client's workspace and overcomes potential compliance barriers by setting conditional access to specific types of coach and/or client data. This improves the field expert-guided decision making by arming experts with additional tools, information, and history of previous engagement within the context of a collaborator application rather than spanning across multiple disparate systems. This allows a client to receive integrated support for complex decisions that require collaboration amongst multiple experts that may sit across organizational and regulatory silos (thus requiring different access levels to data). This can lead to better decisions for clients, less errors caused by translating information from system to system, and contextual information to be maintained across client interactions (thus providing a more seamless support experience for clients).

FIG. 8 is a flow diagram of a connection setup process 800 for one client and multiple coaches in accordance with some embodiments. In this example, a client using client device 102 opens the collaboration application 230 and is connected with two coaches (104-1 and 104-2) via the server 122. While two coaches are described here for illustrative purposes, this example can be extended to more than two coaches.

A client opens (802) the collaborator application and as a result, the server creates (804) a room and places the client in the room (e.g., room 1 502, FIG. 5). When the client requests (806) to be connected with a coach (or multiple coaches), the server receives (808) the connection request and broadcasts (810) the requests to a plurality of coach devices 104. Two coach devices receive (812, 814) the client's request to connect, and each coach device selects (816, 826) the client. Stated another way, a coach associated with each coach device selects the client, and the respective coach devices transmit a selection notification to the server. The server receives (818, 828) the selection notifications from each coach device, and as a result, places (820, 830) the respective coaches into the client's room and transmits (822, 832) notifications to the client device that the respective coaches have joined the room. The client device receives (824, 834) the notifications and displays presence elements for each coach in the client UI indicating presence of the respective coaches in the room. As such, multiple coaches are connected with a single client simultaneously. These operations correspond to operations 602-622 as described above with reference to FIG. 6 (with the addition of a second coach).

FIGS. 9A-9C are flow diagrams of an interaction process 900 between one client and multiple coaches in accordance with some embodiments. In this example, a client using client device 102 interacts with the collaboration application (e.g., enters data) and the server forwards the interaction to two coaches using first and second coach devices 104-1 and 104-2 (FIG. 9A). One coach performs an action (e.g., manipulates the data and/or navigates to a new page) based on the client's interaction (FIG. 9B), and the server forwards the coach's action to the client and to the other coach (FIG. 9C).

More specifically, the client enters data (902), and the client device automatically notifies (904) the server of a data change with a copy of the data. The server receives (906) the data change notification including the data, stores (908) a copy of the data in the database, records (910) actions of the client in the database to preserve for later audit, and broadcasts (912) a data change command notification with a copy of the data to a plurality of coaches. Two coaches receive (914, 916) the data change command notification and update (918, 920) local versions of the client's data and respective coach interfaces in order to synchronize the data and interfaces with those of the client. As such, multiple coaches are synchronized with the client via real time event propagation. These operations correspond to operations 702-716 as described above with reference to FIG. 7A (with the addition of a second coach).

A first of the two coaches (104-1) performs (922) an action (e.g., manipulates data or navigates to a new page). In some embodiments, the actions available to the coach are role specific pre-defined actions (different coaches may have different roles and/or expertise). The first coach continues to perform actions (e.g., manipulates data or navigates to new pages) until the coach is satisfied. Upon selection of an "update" affordance in the coach UI, the coach device notifies (926) the server of the results of the coach actions (e.g., transmits data change command with a copy of the changed data). The server receives (928) the notification from the first coach device, stores (930) a copy of the data or other information associated with the coach's action(s) in the database, and records (932) the coach's actions to preserve for later audit. The server broadcasts (934) one or more data change command notifications (and/or one or more navigation command notifications) to the client device 102 and to the second coach device 104-2. The client device and second coach device receive (936, 938) the notification and each update (940, 942) respective local client data and user interfaces to synchronize the respective devices with the first coach. As discussed above, unlike screen sharing or co-browsing, multiple changes by the coach are propagated at once to avoid cognitive load on the client. Further, compliance requirements are met by keeping an audit trail as needed. Lastly, the client data is synchronized with each of the plurality of coaches who are collaborating simultaneously with the client, allowing for a more seamless collaboration. These operations correspond to operations 718-734 as described above with reference to FIG. 7B and/or operations 736-748 as described above with reference to FIG. 7C (with the addition of a second coach).

Multiple Clients, One Coach

Exemplary solutions for joining multiple clients with a coach disclosed herein, in contrast to co-browsing applications, do not require a one-to-one connection to provide real-time manipulation and editing of a user's information by an expert, or in contrast to screen sharing, do not require a many-to-one broadcast of non-personalized presentations. This promotes the ability for personalized, real-time interactions. In some embodiments, these solutions do not mirror the same user interface across client and coach devices, and thus does not require an expert to go into each individual account to update changes. Accordingly, opportunities for real-time personalization functionality in the context of a collaboration between a coach and multiple clients is provided.

Exemplary techniques described herein use a bi-directional, event-based architecture which facilitates the creation and propagation of "commands" that have the ability to edit/modify UI elements, navigate to different sections of an application, and conditionally manipulate data specific to each client device. This enables coaches to send commands that can be propagated to and interpreted by multiple devices subscribed to an active workspace which can trigger unique and specific actions relevant to each client device, allowing real-time personalization and collaboration across multiple users. In some implementations, this allows a coach device to take one action which can create personalized updates and/or modifications of multiple client devices in real time (or near real time). Moreover, this eliminates scalability constraints other applications face by, for example, using event-based, bi-directional propagation and interpretation of commands which can conditionally modify multiple client devices in real time (or near real time). This further enables the coach collaborator application to be optimized for providing personalized decision support for many users at the same time, including users who have different underlying data and may require different types of visualizations to be supported in their decisions. Updates made by the coach trigger personalized changes to information and navigation unique to each client. This improves the field expert-guided decision making by allowing organizations to bring personalized expertise to more individuals in situations where personalized, iterative support was not previously possible (e.g., lack of personalized support in large webinars).

Figure 10A:
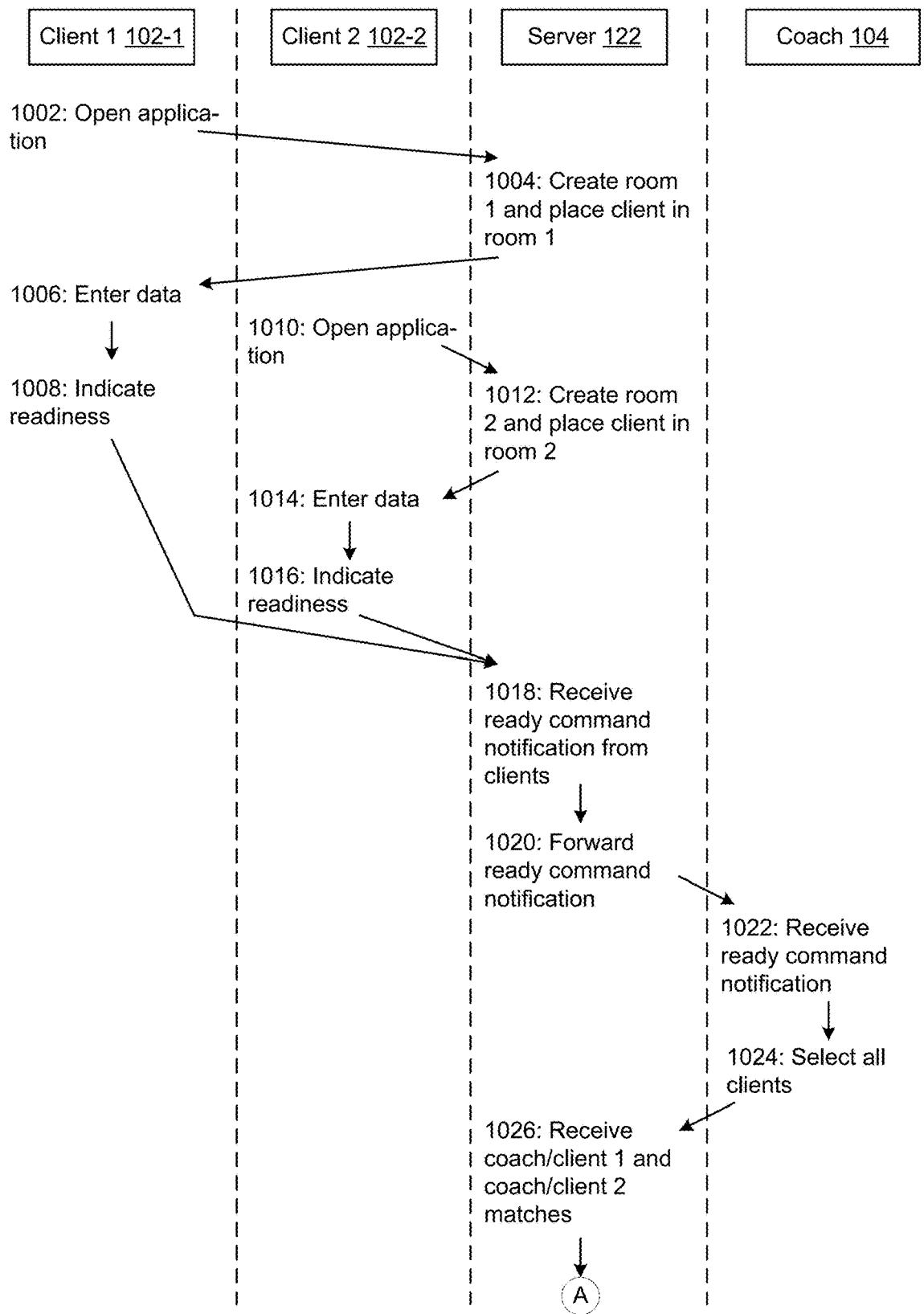
FIGS. 10A-10B are flow diagrams of a connection setup for multiple clients and one coach in accordance with some embodiments.
Figure 10B:
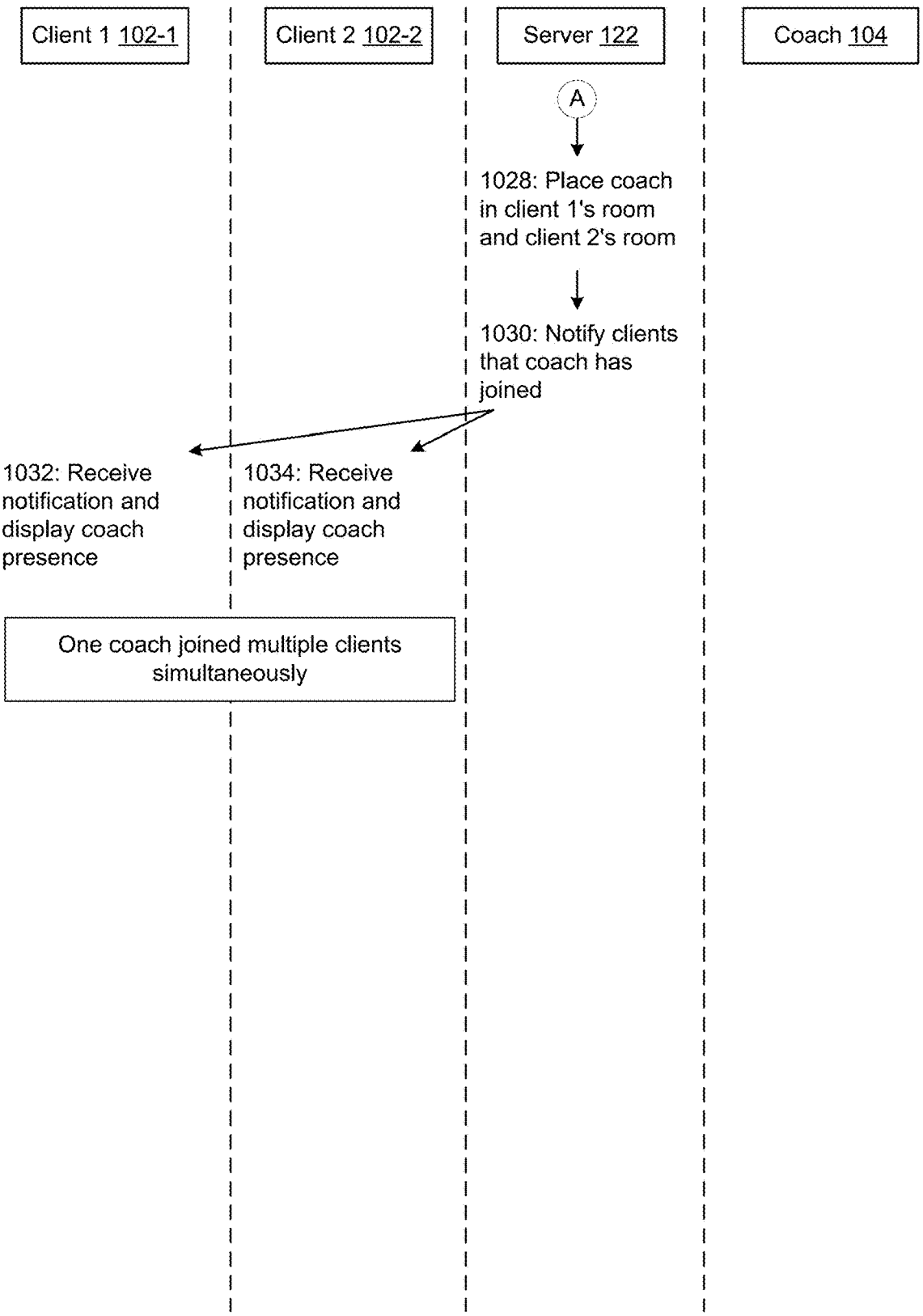

FIGS. 10A-10B are flow diagrams of a connection setup process 1000 for multiple clients and one coach in accordance with some embodiments. In some embodiments, this process is used as a virtual training scenario, during which a coach trains or otherwise collaborates with a plurality of clients. In this example, two clients (102-1, 102-2) open collaborator applications 230 and a server forwards notifications associated with the clients to a coach, who selects the two clients to collaborate with (FIG. 10A). The server places the coach into each client's room and notifies the clients of the coach's presence (FIG. 10B).

Specifically, two clients open (1002, 1010) respective collaborator applications 230 on respective client devices. These operations may be executed in parallel or in sequence. As a result of the collaborator applications being opened, the client devices transmit notifications to the server, and the server creates (1004, 1012) respective rooms for each client. The server places the first client (102-1) into a first room, and the second client (102-2) into a second room different from the first. The clients enter data (1006, 1014) and as a result, the respective client devices indicate readiness (1008, 1016), which includes transmitting ready command notifications to the server. The server receives (1018) the ready command notifications from the clients and forwards (1020) a ready command notification to the coach. The coach receives (1022) the ready command notification (including information indicating availability of each client), and the coach selects (1024) each client, resulting in the coach device sending one or more client match notifications to the server. The server receives (1026) the match notification(s) indicating matches between (i) the coach and the first client, and (ii) the coach and the second client. As a result, the server places (1028) the coach in the first client's room and in the second client's room. The server notifies (1030) both client devices that the coach has joined their respective rooms. The client devices receive (1032, 1034) the notification and display coach presence to the respective clients via the client UIs. As such, one coach has joined multiple clients simultaneously (or otherwise close in time relative to the beginning of the interaction described below). These operations correspond to operations 602-622 as described above with reference to FIG. 6 (with the addition of a second client).

Figure 11A:
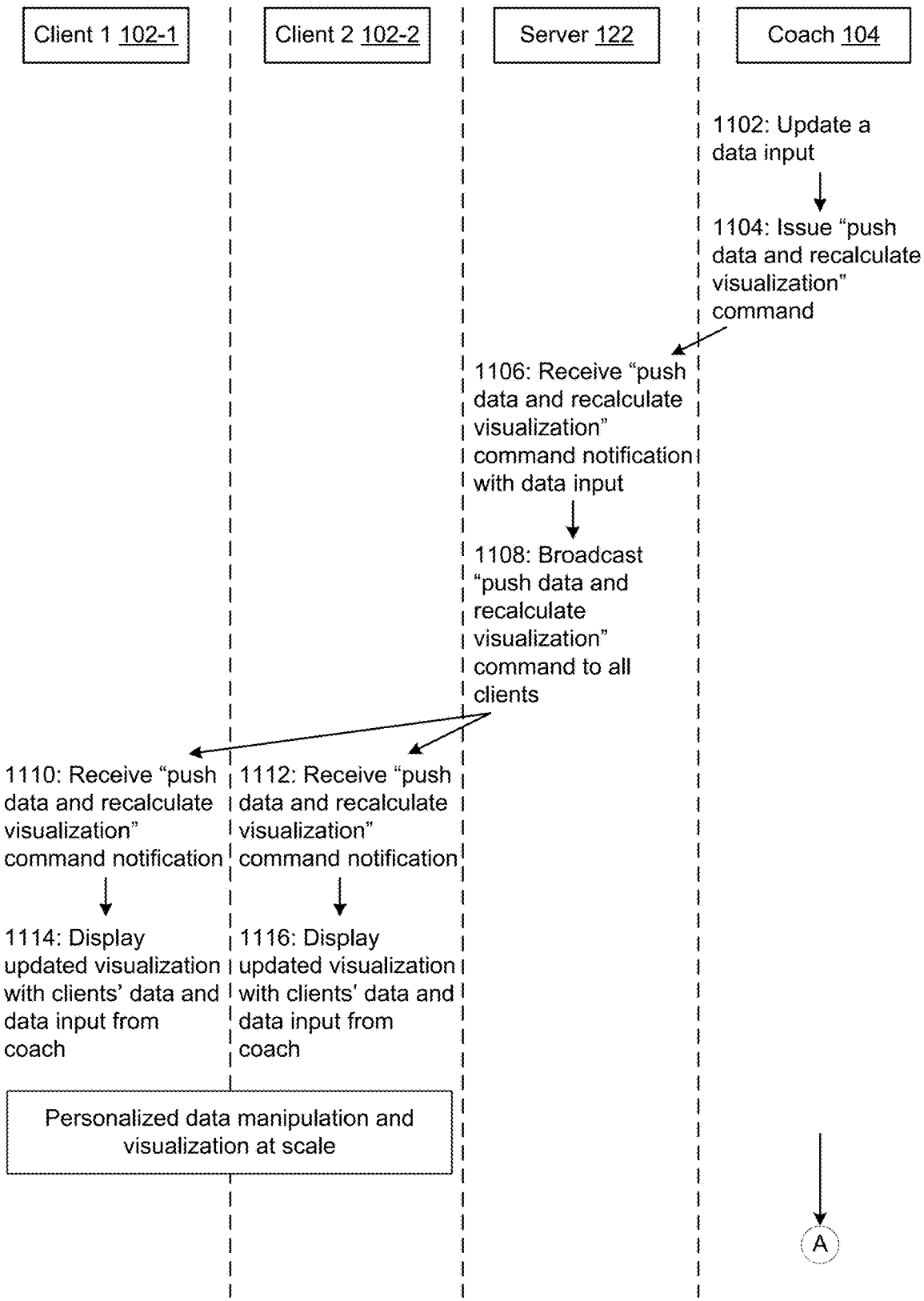
FIGS. 11A-11B are flow diagrams of an interaction between multiple clients and one coach in accordance with some embodiments.
Figure 11B:
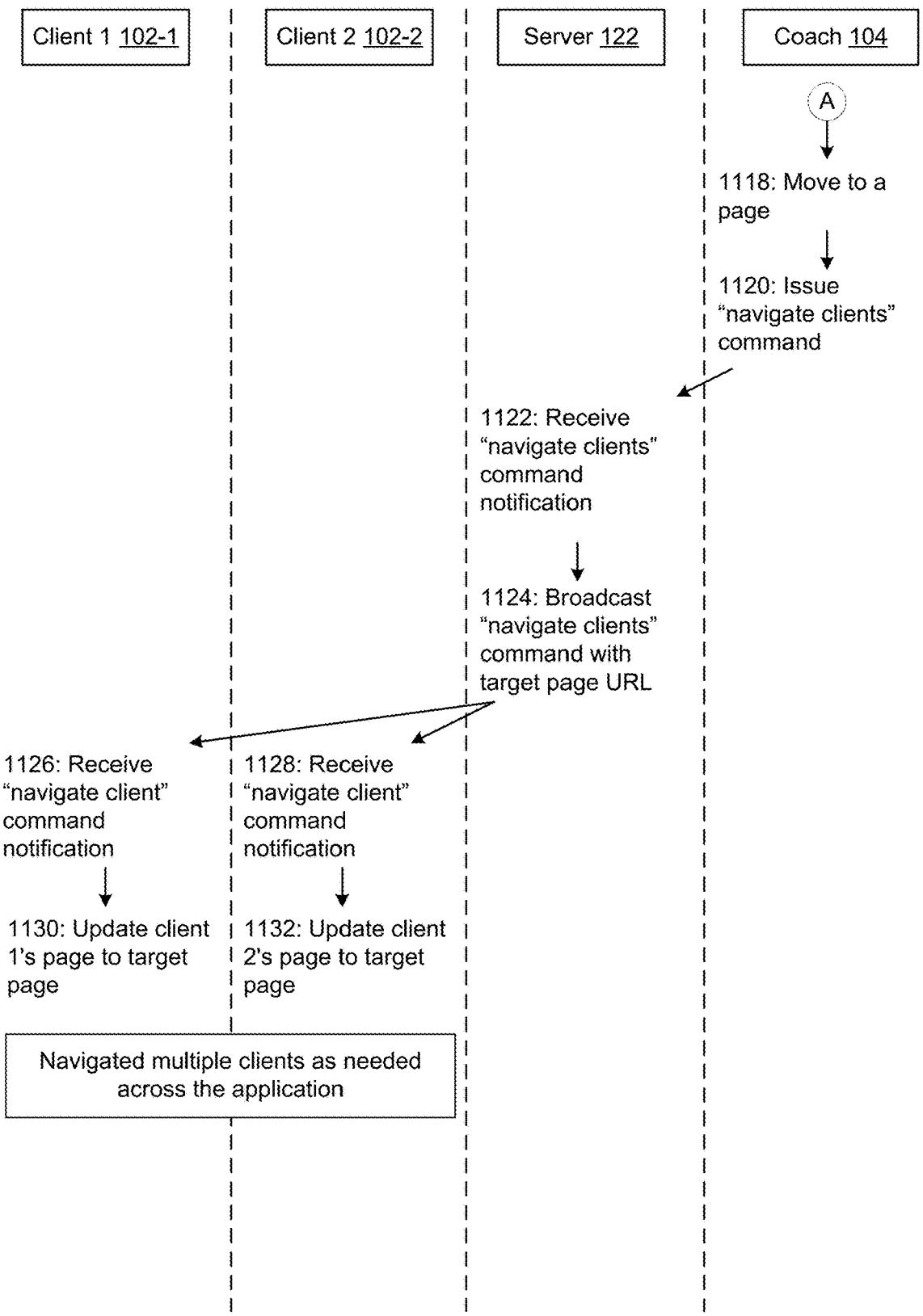

FIGS. 11A-11B are flow diagrams of an interaction process 1100 between multiple clients and one coach in accordance with some embodiments. In some embodiments, this process is used as a virtual training scenario, during which a coach trains or otherwise collaborates with a plurality of clients. In this example, the coach performs an action, such as updating or manipulating data (FIG. 11A) or navigating to a new page (FIG. 11B), and the server notifies both clients of the coach's action.

Specifically, the coach updates (1102) a data input and as a result, the coach device transmits (1104) a "push data and recalculate visualization" command notification, including the updated data, to the server. The server receives (1116) the command notification and updated data, and broadcasts (1108) the command and data to each client device. The two client devices receive (1110, 1112) the command notification and data, and display an updated visualization with each respective client's data along with the updated data from the coach. As such, the coach may provide personalized data manipulation and visualizations at scale (to a plurality of clients). Since each client likely has different data, the coach's updated data will likely result in different visualizations based on the respective client's data. These operations correspond to operations 718-734 as described above with reference to FIG. 7B (with the addition of a second client).

The coach may additionally or alternatively move (1118) or otherwise navigate to a new page. As a result, the coach device issues (1120) a "navigate clients" command and transmits the command to the server. The server receives (1122) the command notification and broadcasts (1124) the command with information identifying the new page (e.g., the target page URL). Each client device receives (1126, 1128) the command notification and updates (1132) the respective client's page to the target page. As such, the coach may navigate multiple clients as needed across the application. These operations correspond to operations 736-748 as described above with reference to FIG. 7C (with the addition of a second client).

User Interfaces

User interface solutions often create a tension between (i) providing a simple interface for users and (ii) providing a robust set of tools for experts to be efficient. Technologies that either broadcast a display of one device's interface to another (i.e., screen sharing) or enable a joint navigation of an interface across multiple devices (i.e., co-browsing) forces collaboration between users and experts across the same interfaces, thus not allowing these applications to tailor collaboration experiences to the specific, differing needs of the parties involved in the collaboration.

Exemplary techniques described herein use a bi-directional, event-based information exchange where collaboration is facilitated through the real-time propagation of commands and data synchronization across client and coach devices subscribed to an active workspace (i.e., room) where each device's interface and functionality is tailored to either the client or the coach (rather than a one-size-fits-all interface). This overcomes current limitations by facilitating collaboration through this bi-directional, event-based exchange, rather than at the user interface level, thus decoupling the display of information from the mechanism in which collaboration is facilitated. Moreover, this enables the ability for any given client device and/or coach device to collaborate on the same underlying data model while tailoring role-specific, dynamic interfaces that can be optimized based on the needs of each user and the conversation taking place. This improves the field of expert-guided decision making by allowing for simpler and more intuitive user interfaces for client devices which increase comprehension while simultaneously enabling coach devices with more robust functionality, visualizations, and role-based controls that increase the speed and effectiveness of collaborations.

Figure 12:
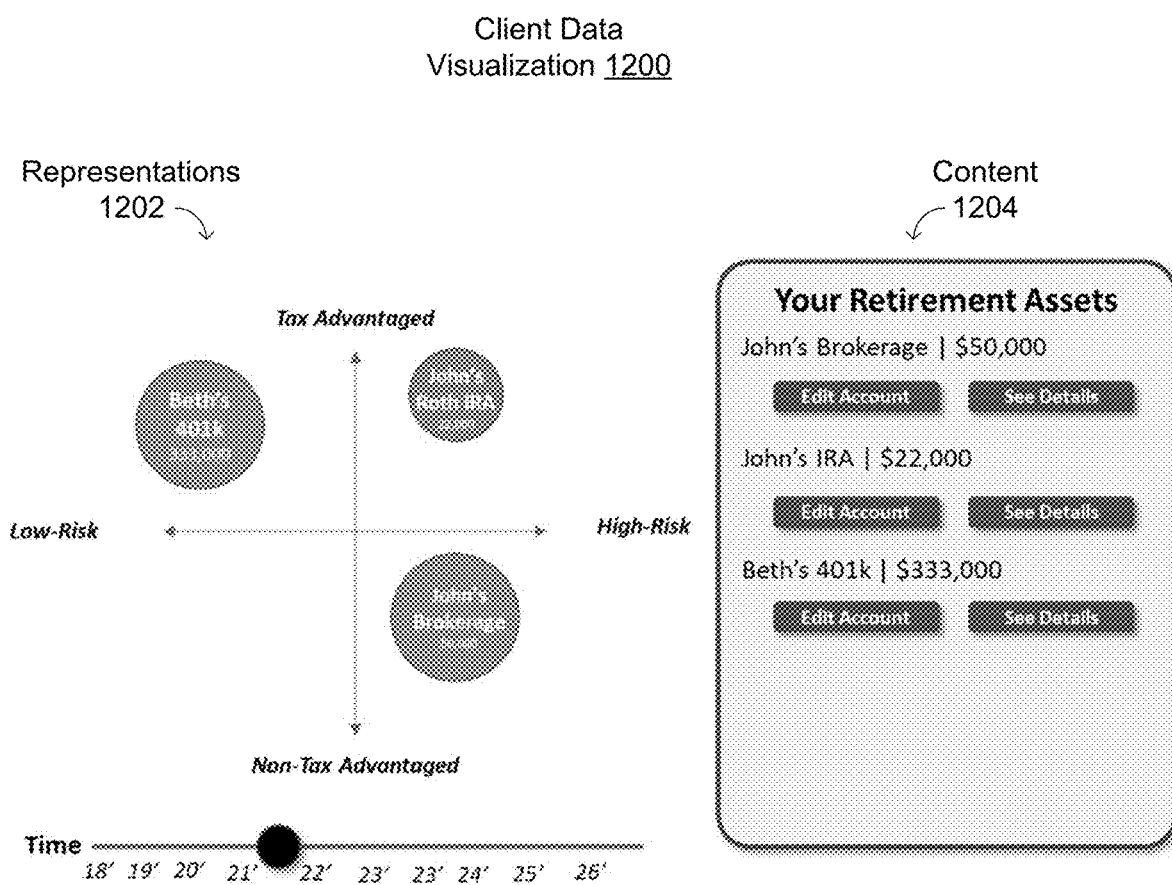
FIG. 12 is a diagram of an example visualization of a client's data in accordance with some embodiments.

FIG. 12 is a diagram of an example visualization 1200 of a client's data in accordance with some embodiments. In this example, the visualization includes data representations 1202 including a chart and a timeline. Content 1204 is associated with the representations 1202. In some embodiments, the content 1204 affects how the representations 1202 are displayed. For instance, if the client enters or updates retirement values associated with a 401k, the element in the chart which represents that value may be updated accordingly.

Figure 13A:
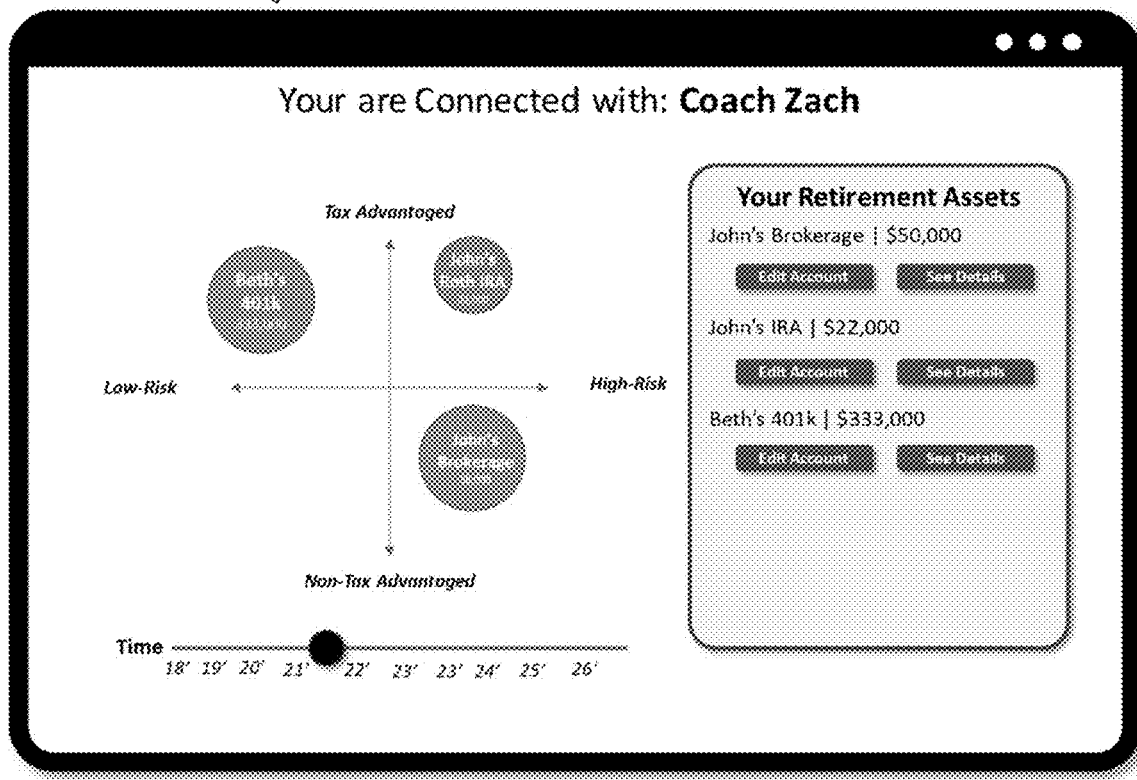
FIGS. 13A-13B are example user interfaces for a client device and a coach device in accordance with some embodiments.
Figure 13B:
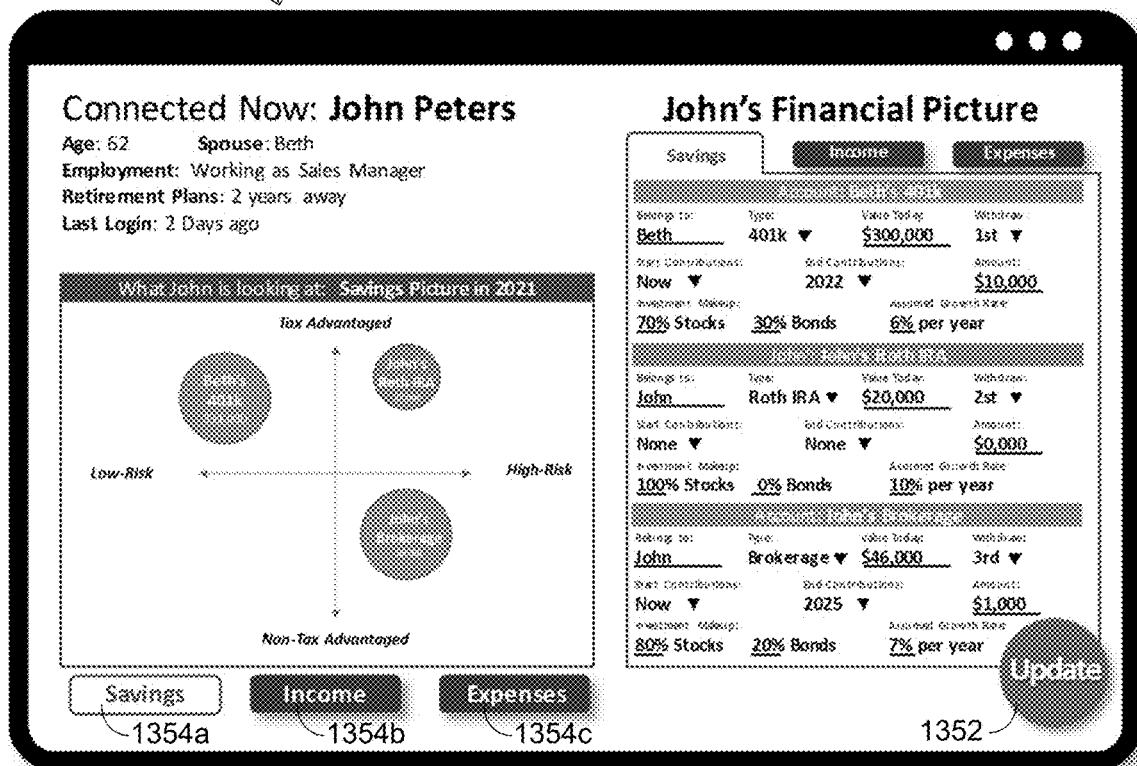

FIGS. 13A-13B are example user interfaces for a client device 102 (interface 1300) and a coach device 104 (interface 1350) in accordance with some embodiments. In some embodiments, the coach UI includes one or more elements not included in the client UI. For example, the coach UI includes various elements (e.g., data input elements, update affordance 1352, navigation elements 1354a-c, and so forth), not viewable or otherwise available to the client, that allow the coach to manipulate the client's data or navigate the client to a new page. As discussed above, changes made at the client UI 1300 may be propagated to the coach UI 1350 in real time (or near real time). However, changes made at the coach UI 1350 may be propagated to the client UI 1300 upon the coach's selection of an "update" affordance 1352 or a "navigate" affordance 1354a-c, at which time, a plurality of updates are propagated to the client UI 1300 (in accordance with the coach's update command) or a new client UI 1300 associated with a new page is displayed (in accordance with the coach's navigation command). As can be seen in FIGS. 13A-13B, bi-directional, event-based exchange enables real-time collaboration across distinctly different interfaces, removing the tension between creating simple interfaces for users and robust sets of tools for experts.

Miscellaneous

The terminology used in the description of the various described implementations herein is for the purpose of describing particular implementations only and is not intended to be limiting. As used in the description of the various described implementations and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof. Additionally, it will be understood that, although the terms "first," "second," etc. may be used herein to describe various elements, these elements should not be limited by these terms. These terms are only used to distinguish one element from another.

As used herein, the term "if" is, optionally, construed to mean "when" or "upon" or "in response to determining" or "in response to detecting" or "in accordance with a determination that," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]" or "in accordance with a determination that [a stated condition or event] is detected," depending on the context.

It is to be appreciated that "smart home environments" may refer to smart environments for homes such as a single-family house, but the scope of the present teachings is not so limited. The present teachings are also applicable, without limitation, to duplexes, townhomes, multi-unit apartment buildings, hotels, retail stores, office buildings, industrial buildings, and more generally any living space or work space.

The foregoing description, for purpose of explanation, has been described with reference to specific embodiments. However, the illustrative discussions above are not intended to be exhaustive or to limit the claims to the precise forms disclosed. Many modifications and variations are possible in view of the above teachings. The embodiments were chosen and described in order to best explain principles of operation and practical applications, to thereby enable others skilled in the art.

Although various drawings illustrate a number of logical stages in a particular order, stages that are not order dependent may be reordered and other stages may be combined or broken out. While some reordering or other groupings are specifically mentioned, others will be obvious to those of ordinary skill in the art, so the ordering and groupings presented herein are not an exhaustive list of alternatives. Moreover, it should be recognized that the stages can be implemented in hardware, firmware, software or any combination thereof.

The above description, for purpose of explanation, has been described with reference to specific implementations. However, the illustrative discussions above are not intended to be exhaustive or to limit the scope of the claims to the precise forms disclosed. Many modifications and variations are possible in view of the above teachings. The implementations were chosen in order to best explain the principles underlying the claims and their practical applications, to thereby enable others skilled in the art to best use the implementations with various modifications as are suited to the particular uses contemplated.

What is claimed is:

1. A method, comprising:
   at a server system including one or more processors:
   receiving a connection request from a client device;
   creating a first digital workspace;
   establishing a first connection with the client device, including populating a first user interface of the client device, wherein the first user interface of the client device corresponds to the first digital workspace;
   broadcasting availability of the client device to a first coach devices;
   in response to the broadcast of availability of the client device, receiving a connection request from the first coach device;
   in response to receiving the connection request from the first coach device, establishing a second connection with the first coach device, including populating a second user interface of the first coach device, wherein the second user interface corresponds to the first digital workspace; and
   transforming client data inputted into the first user interface from a first format to a second format for displaying on the second user interface;
   in accordance with a determination that the client device is associated with a previous digital workspace established during a previous session with the client device:
   accessing the previous digital workspace established during the previous session with the client device;
   establishing a third connection with the client device, including populating the first user interface of the client device with data received during the previous session with the client device;
   broadcasting availability of the client device to two or more coach devices;
   in response to the broadcast of availability of the client device, receiving a connection request from a second coach device of the two or more coach devices; and
   in response to receiving the connection request from the second coach device, establishing a fourth connection with the second coach device, including populating the second user interface of the second coach device, wherein the second user interface corresponds to the previous digital workspace established during the previous session with the client device and includes an element not included in the first user interface of the client device.

2. The method of claim 1, further comprising:
   at the server system:
   receiving, via the first connection, first user data from the client device; and
   updating the first digital workspace based on the received first user data, wherein updating the first digital workspace based on the received first user data includes causing the second user interface of the first coach device to be automatically updated based on the first user data.

3. The method of claim 2, further comprising:
   at the server system:
   receiving, via the second connection, a first coach interaction from the first coach device, wherein the first coach interaction includes two or more workspace actions; and
   updating the first digital workspace based on the received first coach interaction, wherein updating the first digital workspace based on the received first coach interaction includes causing the first user interface of the client device to be automatically updated based on the two or more workspace actions.

4. The method of claim 3, wherein the first coach interaction is received in response to an update command.

5. The method of claim 3, wherein one of the two or more workspace actions includes coach data based on the first user data, and updating the first digital workspace based on the received first coach interaction includes populating the first user interface with the coach data.

6. The method of claim 3, wherein one of the two or more workspace actions includes a navigation command pointing to a third user interface of the client device, and updating the first digital workspace based on the received first coach interaction includes causing the client device to navigate from the first user interface to the third user interface.

7. The method of claim 3, wherein the two or more workspace actions are received simultaneously.

8. The method of claim 5, wherein the two or more workspace actions are received only upon an update command being entered at the first coach device.

9. The method of claim 5, further comprising:
at the server system:
receiving, from the client device, a request to terminate the first connection;
in response to receiving the request to terminate the first connection:
saving the user data and the coach data with the first digital workspace;
transmitting, via the second connection, a session termination notification to the first coach device; and
terminating the first connection with the client device.

10. The method of claim 5, wherein the user data is financial data of a user of the client device, and the coach data includes a result of a calculation or projection based on the financial data of the user of the client device.

11. The method of claim 10, wherein the financial data of the user of the client device includes healthcare data, behavioral data, commercial data, and/or operational data of the user.

12. The method of claim 1, further comprising:
at the server system:
in response to the broadcast of availability of the client device, receiving a connection request from a second coach device; and
in response to receiving the connection request from the second coach device, establishing a third connection with the second coach device, including populating a third user interface of the second coach device, wherein the third user interface corresponds to the first digital workspace and includes a graphical element not included in the first user interface of the client device.

13. The method of claim 12, further comprising:
at the server system:
receiving, via the first connection, first user data from the client device; and
updating the first digital workspace based on the received first user data, wherein updating the first digital workspace based on the received first user data includes causing (i) the second user interface of the first coach device to be automatically updated based on the first user data and (ii) the third user interface of the second coach device to be automatically updated based on the first user data.

14. The method of claim 12, further comprising:
at the server system:
receiving, via the second connection, a first coach interaction from the first coach device, wherein the first coach interaction includes two or more workspace actions; and
updating the first digital workspace based on the received first coach interaction, wherein updating the first digital workspace based on the received first coach interaction includes causing (i) the first user interface of the client device to be automatically updated based on the two or more workspace actions and (ii) the third user interface of the second coach device to be automatically updated based on the two or more workspace actions.

15. The method of claim 1, wherein the client device is a first client device and the method further comprises:
at the server system:
establishing a third connection with a second client device, including populating a third user interface of the second client device, wherein the third user interface corresponds to a second digital workspace;
broadcasting availability of the second client device to two or more coach devices;
in response to the broadcast of availability of the second client device, receiving a connection request from the first coach device of the two or more coach devices; and
in response to receiving the connection request from the first coach device, updating the second user interface of the first coach device to correspond to the digital workspace and the second digital workspace, wherein the second user interface includes an element not included in the first user interface of the first client device or the third user interface of the second client device.

16. The method of claim 15, further comprising:
at the server system:
receiving, via the second connection, a first coach interaction from the first coach device, wherein the first coach interaction includes two or more workspace actions; and
updating the first digital workspace and the second digital workspace based on the received first coach interaction, wherein updating the first digital workspace and the second digital workspace based on the received first coach interaction includes causing the first user interface of the first client device and the third user interface of the second client device to be automatically updated based on the two or more workspace actions.

17. The method of claim 15, further comprising:
at the server system;
in response to the broadcast of availability of the first client device or the second client device, receiving a connection request from a second coach device of the two or more coach devices; and
in response to receiving the connection request from the second coach device, establishing a fourth connection with the second coach device, including populating a fourth user interface of the second coach device, wherein the fourth user interface corresponds to the first digital workspace and the second digital workspace and includes the element not included in the first user interface of the first client device or the third user interface of the second client device.

18. A system including one or more processors and memory storing one or more programs to be executed by the one or more processors, the one or more programs including instructions for executing the method of claim 1.

19. A non-transitory computer readable storage medium storing one or more programs configured for execution by a computer system, the one or more programs including instructions for executing the method of claim 1.

* * * * *